US011274295B2

(12) United States Patent
Mikkelsen et al.

(10) Patent No.: US 11,274,295 B2
(45) Date of Patent: Mar. 15, 2022

(54) METHODS FOR GENERATING POOLS OF VARIANTS OF A DNA TEMPLATE

(71) Applicant: The Broad Institute, Inc., Cambridge, MA (US)

(72) Inventors: Tarjei Mikkelsen, Cambridge, MA (US); Alexandre Melnikov, Bellingham, MA (US)

(73) Assignee: THE BROAD INSTITUTE, INC., Cambridge, MA (US)

( * ) Notice: Subject to any disclaimer, the term of this patent is extended or adjusted under 35 U.S.C. 154(b) by 648 days.

(21) Appl. No.: 14/420,881

(22) PCT Filed: Aug. 9, 2013

(86) PCT No.: PCT/US2013/054358
§ 371 (c)(1),
(2) Date: Feb. 10, 2015

(87) PCT Pub. No.: WO2014/026123
PCT Pub. Date: Feb. 13, 2014

(65) Prior Publication Data

US 2015/0203838 A1 Jul. 23, 2015

Related U.S. Application Data

(60) Provisional application No. 61/681,878, filed on Aug. 10, 2012.

(51) Int. Cl.
*C12N 15/10* (2006.01)
*C12N 15/63* (2006.01)

(52) U.S. Cl.
CPC ..... *C12N 15/1027* (2013.01); *C12N 15/1031* (2013.01); *C12N 15/1058* (2013.01); *C12N 15/1079* (2013.01)

(58) Field of Classification Search
CPC ............ C12N 15/1027; C12N 15/1031; C12N 15/1058; C12N 15/1079
See application file for complete search history.

(56) References Cited

U.S. PATENT DOCUMENTS

2006/0223081 A1* 10/2006 Jarrell ................ C12N 15/1031 435/6.1
2011/0082055 A1* 4/2011 Fox ...................... C12N 15/102 506/17

FOREIGN PATENT DOCUMENTS

WO WO 02/44361 A2 6/2002
WO WO-2012154201 A1 * 11/2012 ........... C12Q 1/6834
WO WO-2013003290 A1 * 1/2013 ......... C12N 15/1027

OTHER PUBLICATIONS

European Office Action for counterpart European Patent Application No. 13753008.5, dated May 4, 2016, 3 pages.
International Preliminary Report on Patentability for PCT Application No. PCT/US2013/054358, dated Feb. 10, 2015, 5.
Office Action for European Patent Application No. 13753008.5, dated Nov. 3, 2016, 4.

(Continued)

*Primary Examiner* — Jeremy C Flinders
(74) *Attorney, Agent, or Firm* — Johnson, Marcou, Isaacs & Nix LLC; F. Brent Nix, Esq.; Michael B. Scher, Esq.

(57) ABSTRACT

The invention provides methods for generating pools of variants of DNA templates, and methods of using pools of variants to identify sequences involved in conferring sensitivity or resistance to environmental factors.

18 Claims, 19 Drawing Sheets

(56) References Cited

OTHER PUBLICATIONS

Nassal, et al., "PCT-Based Site-Directed Mutagenesis Using Primers with Mismatched 3'-Ends", Nucleic Acids Research, vol. 18, No. 10, Jan. 1, 1990, 3077-3078.

International Search Report and Written Opinion dated Nov. 4, 2013 for PCT/SE2013/054358, 4 pages.

Saboulard, D. et al., "High-Throughput Site-Directed Mutagenesis Using Oligonucleotides Synthesized on DNA Chips," Biotechniques, Informa Healthcare, Sep. 1, 2005, vol. 39, No. 3, pp. 363-368.

Kunkel, T. et a., "Rapid and Efficient Site-Specific Mutagenesis Without Phenotypic Selection," Proceedings of the National Academy of Sciences, PNAS, National Academy of Sciences, Jan. 1, 1985, vol. 82, No. 1, pp. 488-492.

Iba, Y et al., "Expression Vectors for the Introduction of Highly Diverged Sequences into the Six Complementarity-Determining Regions of an Antibody," Gene, Elsevier, Jul. 18, 1997, vol. 194, No. 1, pp. 35-46 (abstract only).

"European Office Action for European Patent Application No. 13753008.5", dated Sep. 6, 2017.

Leproust, et al., "Synthesis of High-Quality Libraries of Long (150mer) Oligonucleotides by a Novel Deprivation Controlled Process", Nucleic Acids Research, vol. 38, No. 8, 2010, 2522-40.

Melnikov, et al., "Rapid dissection and model-based optimization of inducible enhancers in human cells using a massively parallel reporter assay", Nature Biotechnology, vol. 30, 2012, 271-277.

* cited by examiner a

Kanamycin A (CID 6032)

Ribostamycin (CID 33042)

G418 (CID 123865)

Amikacin (CID 37768)

Neomycin B (CID 8378)

Paromomycin (CID 165580)

b a b

| Pos | Cons. score | $log_{10}$ ΔMut (rep. 1) | $log_{10}$ ΔMut (rep. 2) | WT | Tolerated (rep. 1) | Tolerated (rep. 2) |
|---|---|---|---|---|---|---|
| 192 | -1.04 | +0.54 | +0.60 | C | IKT | IT |
| 231 | -0.77 | +0.41 | +0.11 | E | FHIRWY | FHRY |
| 256 | -0.52 | +0.31 | +0.21 | F | W | WY |
| 162 | -0.49 | +0.37 | +0.30 | H | N | N |
| 137 | -0.48 | +0.40 | +0.21 | A | FILMRVY | FILMRVY |
| 52 | -0.46 | +0.70 | +0.41 | D | ACEGIQSTV | ACEIQSTV |
| 191 | -0.36 | +0.14 | +0.31 | A | CFH | F |
| 158 | -0.33 | +1.14 | +0.96 | L | FWY | FWY |
| 33 | -0.28 | +0.40 | +0.26 | D | GNPST | AGQRST |
| 234 | -0.24 | +0.58 | +0.30 | G | ADEHIKMNP... | ADEKMPQRST |
| 178 | -0.10 | +0.25 | +0.13 | M | CEFQRVWY | CFHKLQRTY |

Ectopic PPARG- and TZD-dependent differentiation of human SGBS pre-adipocytes

Arg140 to His Phe388 to Leu Phe162 to Val

"Wild-type function" "Partial loss of function" "Loss of function"

Change in mutant frequency after Cd36+ selection

A

Arg140 to His Phe388 to Leu Phe162 to Val

"Wild-type function" "Partial loss of function" "Loss of function"

B

Change in mutant frequency after Cd36+ selection

METHODS FOR GENERATING POOLS OF VARIANTS OF A DNA TEMPLATE

CROSS-REFERENCE TO RELATED APPLICATIONS

This application is the U.S. National Stage of International Application No. PCT/US2013/054358, filed Aug. 9, 2013, published in English under PCT Article 21(2), which claims the benefit of U.S. Ser. No. 61/681,878, filed on Aug. 10, 2012, the contents of which are incorporated herein by reference.

BACKGROUND OF THE INVENTION

Generation of DNA libraries for mutational scanning, directed evolution, and related techniques requires trading-off control over library content against diversity. Traditional site-directed mutagenesis offers a high level of control, but requires one independent reaction per mutation or site, which limits how much diversity can be generated in a cost-efficient manner. Error-prone PCR, spiked oligonucleotide synthesis, and chemical mutagenesis can generate highly diverse libraries in a single reaction, but provide limited control over their contents. In particular, introducing unbiased nucleotide substitutions into a protein-coding sequence produces a highly biased mutational spectrum at the amino acid level, and introducing multiple substitutions into one sequence forces incomplete sampling of the sequence space and may obscure the effect of individual substitutions through non-additive effects.

There is a need for methods of generating mixtures of variants of a template DNA molecule in a short time and in a relatively inexpensive manner, such that the mixtures include, e.g., every possible variant of every nucleotide of the template DNA molecule.

SUMMARY OF THE INVENTION

The invention provides methods of generating mixtures of variants of template DNA molecules. In general, the methods include: a) providing a plurality of oligonucleotides, where each of the oligonucleotides: i) corresponds to a first region of a template DNA molecule, ii) has at least one sequence variation as compared to the sequence of the first region of the template DNA molecule, and, optionally, iii) includes a central region that has the at least one sequence variation and two end regions, wherein the end regions are invariant; b) providing a plurality of linearized plasmid vectors comprising the remainder of the template DNA molecule, but lacking the first region of the template DNA molecule at the ends of the linearized plasmid vectors; and c) joining the plurality of oligonucleotides to the plurality of linearized plasmid vectors, thereby generating plasmids including a mixture of variants of the first region of the template DNA molecule.

In one embodiment of the methods of the invention, the template DNA molecule encodes a polypeptide, a non-coding RNA, or an untranslated regulatory sequence. Additionally or alternatively, the template DNA sequence can include a promoter sequence and/or an enhancer sequence. The variation can be, for example, a substitution of at least one nucleotide (e.g., 1, 2, 3, or more nucleotides). The methods of the invention can, in various examples, include the use of a plurality of oligonucleotides including oligonucleotides encoding at least one variation of every amino acid encoded by the first region of the template DNA molecule.

The methods of the invention also can include: a) providing a second plurality of oligonucleotides, wherein each of the oligonucleotides: i) corresponds to a second region of a template DNA molecule, ii) has at least one sequence variation as compared to the sequence of the second region of the template DNA molecule, and, optionally, iii) includes a central region that has the at least one sequence variation and two end regions, wherein the end regions are invariant; b) providing a plurality of linearized plasmid vectors including the remainder of the template DNA molecule, but lacking the second region of the template DNA molecule at the ends of the linearized plasmid vectors; c) joining the second plurality of oligonucleotides to the plurality of linearized plasmid vectors, thereby generating plasmids including a mixture of variants of the second region of the template DNA molecule; and d) mixing the mixture of plasmids including variants of the first region of the template DNA molecule with the mixture of plasmids including variants of the second region of the template DNA molecule to generate a mixture of variants of the first and second regions of the template DNA molecule. The first and second regions of the template DNA molecule may or may not overlap.

The plurality of oligonucleotides used in the methods of the invention can be oligonucleotides that include at least one or more variations (e.g., one, two, three, or more) of every nucleotide of the first region and/or the second region of the template DNA molecule.

The methods of the invention can be used to generate variants of template DNA molecules which have "n" regions, where "n" is designated arbitrarily and some or all of "n" regions may overlap. In such a case, the method includes performing steps a) to d) mentioned above to generate a mixture of variants of each of the "n" regions. In any of the methods of the invention, "n" can be greater than, e.g., 1, 2, 3, 4, 5, 10, 20, 25, 30, 50, or 100. For example, "n" can be 1, 2, 3, 4, 5, 6, 7, 8, 9, 10, 15, 20, 25, 30, or 50. In various embodiments of the invention, the mixture of plasmids of each of the "n" regions is mixed in equimolar amounts.

The methods of the invention can be used to generate mixtures of variants that include at least one variation (e.g., 1, 2, 3, 4, or more) in every nucleotide along the entire length of a template DNA molecule. The variations in template DNA sequence can be substitutions, insertions, or deletions of one or more nucleotides. If a template DNA molecule encodes a polypeptide, then the variation in amino acid sequence encoded by the template DNA molecule, resulting from the methods of the invention, can encode a naturally occurring amino acid or an unnatural amino acid.

The methods of the invention also include synthesizing a plurality of oligonucleotides, as described herein, on a micro-scale solid support (e.g., a microarray). Oligonucleotides corresponding to overlapping "n" regions can optionally be synthesized on different microarrays. Each oligonucleotide in the above-mentioned plurality of oligonucleotides can be, for example, 150 to 250 nucleotides in length, and the plurality of oligonucleotides can be amplified using the polymerase chain reaction prior to the above-mentioned joining step.

The invention also includes methods of generating linearized plasm id vectors by carrying out the polymerase chain reaction or restriction enzyme digestion reaction prior to the joining step. Prior to the above-mentioned mixing step, the methods can further include: a) transforming into a host cell (e.g., a bacteria or yeast), the mixture of plasmids generated by the joining; b) selecting (e.g., by antibiotic selection or nutrient selection) for recombinant clones containing the plasmids; and c) isolating plasmids containing the variants. The linearized plasmid vectors may, for example, encode an antibiotic selection protein or a protein for nutrient selection, which can be used for selecting recombinant clones.

The invention also includes methods involving generating one or more plasmids in a mixture of plasmids where each plasmid includes one or more variation in two or more different regions of a template DNA molecule. The mixture of plasmids can be generated by creating a first mixture of variant-containing plasmids corresponding to a first region of the template DNA molecule, followed by linearization of the first mixture of variant-containing plasmids and joining of a second plurality of variation-containing oligonucleotides corresponding to a second region of the template DNA molecule to create a mixture of plasmids that includes variations in two different regions of the template DNA molecule. The methods can be used successively to generate mixtures of plasmids wherein each plasmid comprises variations in the 'in' different regions of a template DNA molecule.

The invention also includes methods of generating mixtures of variants of a template DNA molecule by: a) providing a plurality of oligonucleotides, wherein each of the oligonucleotides: i) corresponds to one of multiple regions of the template DNA molecule; ii) has at least one sequence variation as compared to the sequence of the one of multiple regions of the template DNA molecule; and iii) the plurality of oligonucleotides comprises oligonucleotides that correspond to each of the multiple regions of the template DNA molecule; b) providing a plurality of linearized plasmid vectors including the remainder of the template DNA molecule, but lacking the multiple regions of the template DNA molecule as described herein; and c) joining the plurality of oligonucleotides to each other and the plurality of linearized plasmid vectors, thereby generating plasmids including a mixture of variants of the multiple regions of the template DNA molecule. The plurality of oligonucleotides can further include oligonucleotides identical to at least one region of the template DNA molecule and the plurality of oligonucleotides can, optionally, not include oligonucleotides corresponding to the at least one region that have a variation as compared to the template DNA molecule.

In another aspect, the invention includes methods of identifying variant nucleic acid molecules (e.g., molecules encoding proteins, optionally an antibiotic or chemotherapeutic resistance protein) which, when introduced into a cell, selectively increase or decrease the sensitivity of the cell to an environmental factor. These methods include:

a) introducing a mixture of variants of a template DNA molecule (e.g., a mixture generated by any of the foregoing methods) into both a first population of cells and a second population of cells,
b) incubating the first population of cells in the presence of a first environmental factor;
c) incubating the second population of cells in the absence of the first environmental factor;
d) isolating cells exhibiting a phenotype associated with increased or decreased sensitivity to the first environmental factor; and
e) determining which variants of the template DNA molecule are enriched or depleted in cells isolated from the first population of cells as compared to the second population of cells;

thereby identifying variant nucleic acid molecules that selectively increase or decrease the sensitivity of the cells to the first environmental factor.

In certain embodiments, the second population of cells are grown in the presence of a second environmental factor, thereby permitting the identification of variants that selectively increase or decrease the sensitivity of the cells to the first environmental factor relative to the second environmental factor.

In some embodiments, the population of cells are bacterial or fungal cells, and the first environmental factor is, e.g., an antibiotic. When present, a second environmental factor can be, e.g., an antibiotic, optionally an antibiotic from the same family as the first environmental factor.

In other embodiments, the cell populations can be mammalian cells and, e.g., the first environmental factor can be a chemotherapeutic agent. If present, the second environmental factor can be, e.g., a chemotherapeutic agent, optionally a chemotherapeutic agent from the same family as the first environmental factor.

In other embodiments, the environmental factor or factors can be selected from, e.g., cell differentiation agents, antiviral compounds, growth factors, drugs (e.g., anti-cancer agents), nutrients (e.g., carbon sources and vitamins), cellular toxins, anti-aging compounds, anti-fungal compounds, anti-protozoan compounds, hormones, steroids, anti-inflammatory agents, mutagens (e.g., ultraviolet light, X-rays, gamma rays, and chemical carcinogens), temperature, pressure, pH, salinity, viscosity, pathogenic organisms or particles that attach to or enter cells, and components of such organisms or particles that mediate cell entry or other interactions with the host cell.

In any of the foregoing methods, the isolating of cells can include, e.g., collection of surviving cells or separation of cells having a particular morphological characteristic, optionally wherein the morphological characteristic is cell size, expression of a differentiation marker, cell adhesion, or cell membrane integrity. Such separation can include, e.g., fluorescent activation cell sorting (FACS).

Any of the foregoing methods can further include introducing a mixture of variants of a template DNA molecule into a third population of cells, incubating the third population of cells in the presence of a third environmental factor, and determining which variants of the template DNA molecule are enriched or depleted in cells incubated with the third environmental factor as compared to the first and/or second environmental factors, thereby identifying variants that selectively increase or decrease sensitivity of the cells to the third environmental factor.

Also, in any of the foregoing methods, the mixture of variants of a template DNA molecule can be, e.g., encapsulated in a viral particle when introduced into a population of cells. In some embodiments, the methods include isolating cells exhibiting a phenotype associated with increased or decreased sensitivity to the first environmental factor, and further can include isolating viral DNA or RNA from the population of cells.

Definitions

By "template DNA molecule" is meant a DNA polynucleotide that is, in general, 100 or more nucleotides in length (e.g., greater than 100, 150, 200, 300, 500, 800, 1000, 2000, 5000, 10000, or 20000 nucleotides in length, with the option of the upper limit being typically 1 megabase, 100 kb, 50 kb, or 15 kb). Thus, in various examples, the template DNA polynucleotide is 100-20000, 150-5000, 200-2000, 300-1000, or 500-800 nucleotides in length. A template DNA molecule can include, e.g., a sequence that encodes a polypeptide, DNA regulatory element, or RNA, and can be in the form of double or single stranded DNA.

By a "variant" template DNA molecule is meant a template DNA molecule with one or more (e.g., 2, 3, 4, 5, 10, or more) changes in nucleotide sequence relative to an original template DNA molecule. Thus, in various examples, the variant can have 1-20, 2-15, 3-12, 4-10, or 5-8 changes. The variant can be created by substitution, insertion, or deletion of one or more nucleotides within the original template DNA molecule sequence.

A variant is "enriched" in a first population of cells (e.g., an isolated population of cells) relative to a second population of cells if the variant is present at a greater frequency in the first population of cells as compared to the second population of cells.

A variant is "depleted" in a first population of cells (e.g., an isolated population of cells) relative to a second population of cells if the variant is present at a lower frequency in the first population of cells as compared to a second population of cells. A lower frequency includes (but does not require) the complete absence of a particular variant in the first population of cells.

By "oligonucleotide" or "polynucleotide" is meant a polymer of nucleotides, with oligonucleotides in general being relatively short (e.g., 25-500, 100, 150, 200, 250, 300, 350, 400, 450, or 500 nucleotides in length) and polynucleotides being longer. Oligonucleotides and polynucleotides can contain natural or synthetic nucleotides. Unless indicated otherwise, these terms are interchangeable as used herein.

By "linearized plasmid vector" is meant a plasmid vector that is made linear (e.g., by a polymerase chain reaction or by a restriction digestion reaction). The linearized plasmid vector has a 5' end and a 3' end. The 5' and 3' ends can be, e.g., single stranded or blunt.

By "overlap" is meant a region of nucleotide sequence that is identical between two oligonucleotides such that the 5' end of one oligonucleotide has 3 or more nucleotide (e.g., 3, 4, 5, 10 or more) identity to the 3' end of another oligonucleotide.

By "nutrient selection" is meant a technique known in the art for selecting plasmids containing a gene required for the growth and propagation of a bacterium, in a medium which lacks or is supplemented with a specific nutrient.

By "phenotype associated with increased or decreased sensitivity" to an environmental factor is meant a cell characteristic that is associated with exposure to the environmental factor. For example, the phenotype can be expression of a differentiation marker, increase cell growth, increased cell death, or decreased cell growth. Increases in sensitivity result can result in an increase or decrease in the presence of the associate phenotype. Similarly, a decrease in sensitivity can result in an increase or decrease in the presence of the associate phenotype. For example, in cases where the environmental factor is a particular toxic agent, a decrease in sensitivity to the toxic agent produces a phenotype of increased cell survival/growth, while an increase in sensitivity to the toxic agent produced a decrease in cell survival/growth.

By "isolating" is meant separating cells having a certain phenotype from those cells that lack that phenotype. Methods of isolation include physical separation of cells having a phenotype, depletion of cells lacking the phenotype, or enrichment of cells having a phenotype.

By "environmental factor" is meant any aspect of the cell culture conditions that can be controlled by an individual performing the methods of the invention. For example, environmental factors can be the presence or absence of particular nutrients, toxins, antibiotics, anti-viral agents, chemotherapeutic agents, anti-inflammatory agents, vitamins, hormones, differentiation factors, pathogens (including viruses or bacteria), or other cell types (e.g., feeder cells). Environmental factors can also include other aspects of cell culture, including temperature, atmospheric components, atmospheric pressure, electromagnetic radiation (e.g., visible light, UV light, X-rays, or gamma rays), or mechanical vibration.

Other features and advantages of the invention will be apparent from the detailed description, drawings, and claims.

Arrows indicate a rotation of the structure. (f) is a graphs showing specificity towards the indicated aminoglycoside for pairs of synthetic enzyme variants designed to favor (+) or disfavor (−) this substrate over kanamycin, relative to that of WT APH('3)II. Bars show the medians and error bars show the ranges observed over 2-3 independent cultures, bounded by the resolution of the assay (2-fold dilutions). The variant predicted to favor kanamycin over amikacin (Ami.−) showed minimal activity on both substrates. (g) is a pair of graphs showing optical density in *E. coli* cultures transformed with WT APH(3') or synthetic variants designed to specifically favor paromomycin (Paro+) or kanamycin (Paro−), after selection with each of these two aminoglycosides.

Figure 16:
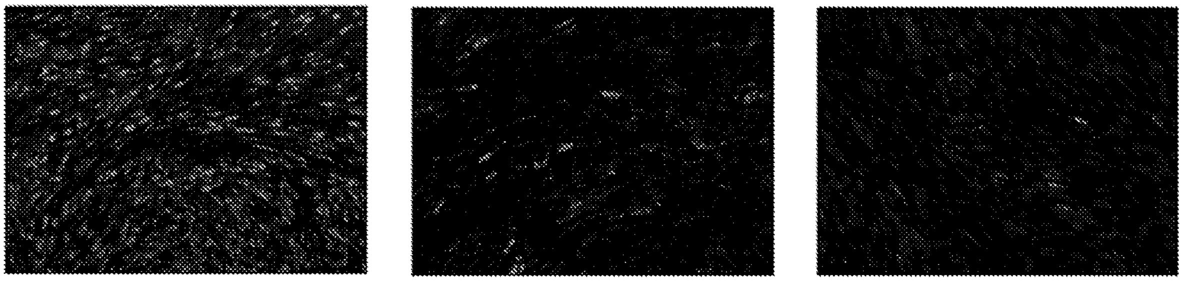

FIG. 16 is a series of images showing presence of an adipocyte differentiation marker (intracellular lipid accumulation) in cells having the indicated mutations.

Figure 17:
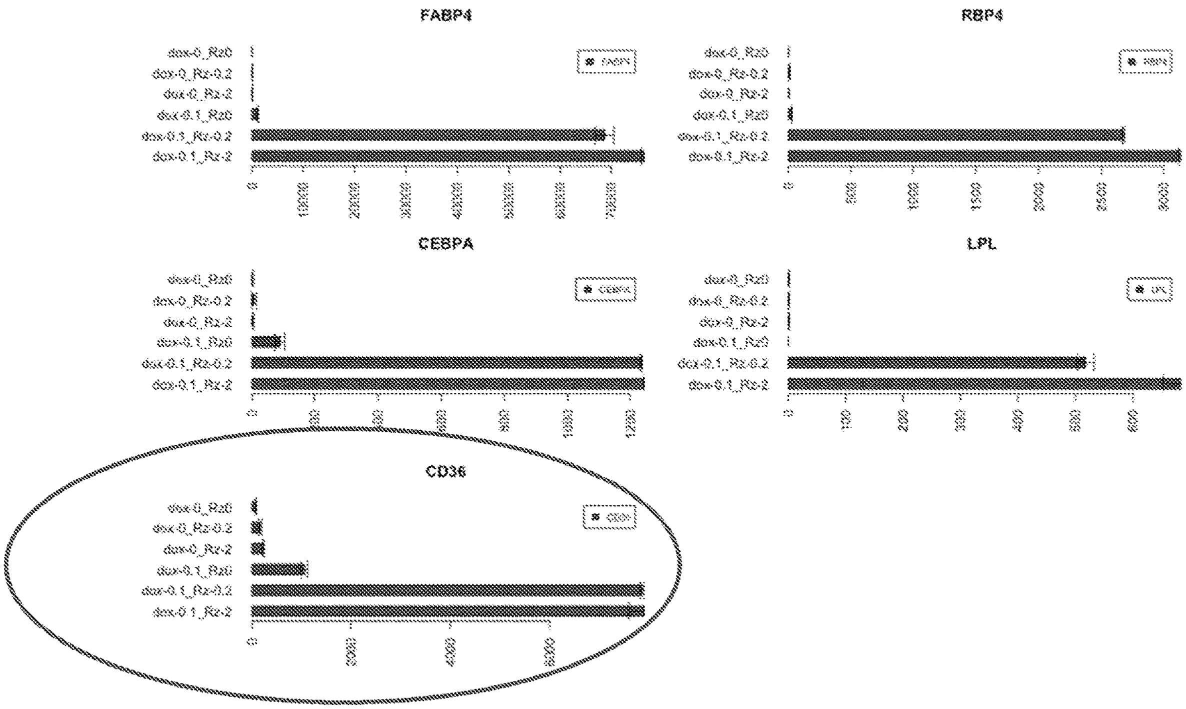

FIG. 17 is a series of graphs showing expression of the indicated gene in the presence and/or absence of doxycycline-induced expression of wild-type PPARγ and rosigliatizone.

Figure 18:
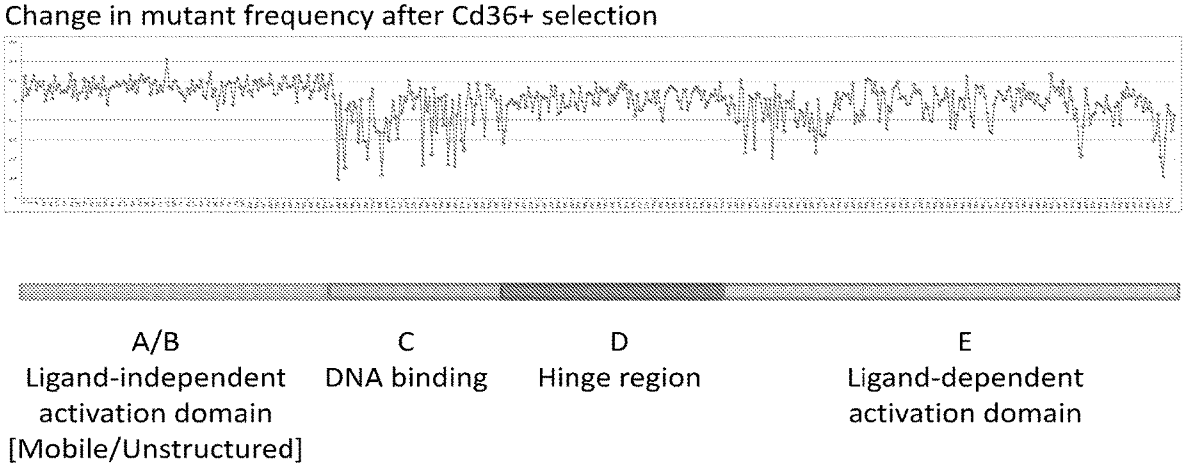
Figure 19:
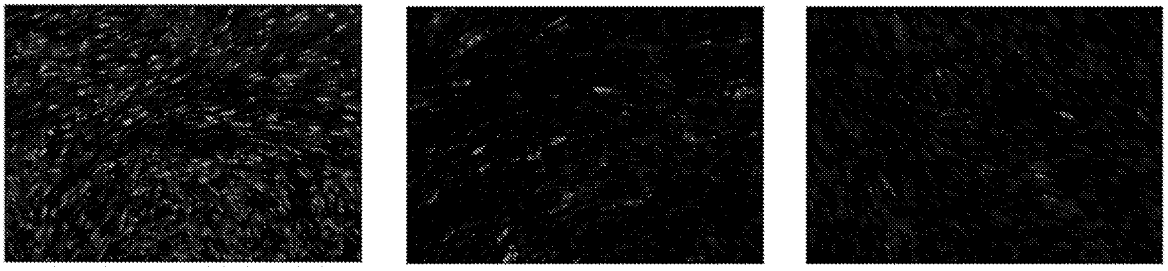
Figure 19:
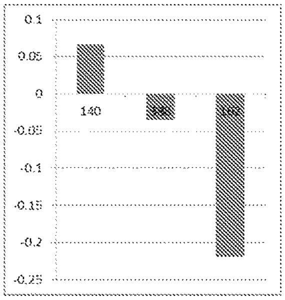

FIG. 18 is a graph showing mutation frequency after Cd36+ selection across the entire human PPARγ protein sequence. The bars indicate the extent of key protein domains.

FIG. **19*a*** is a series of images showing presence of an adipocyte differentiation marker (intracellular lipid accumulation) in cells having the indicated mutations.

FIG. **19*b*** is a graph showing the corresponding change in mutant frequency after Cd36+ selection.

DETAILED DESCRIPTION OF THE INVENTION

The invention provides methods of generating mixtures of nucleic acid (e.g., DNA) molecules (typically in the form of vectors, such as plasmids, e.g., viral vectors), in which each DNA molecule contains, in part, a variant of a common template DNA molecule. The methods of the invention can be used in the construction of mixtures of variants (also referred to herein as mutagenesis libraries) that contain many or all variants of a template DNA molecule. For example, the methods can be used for the construction of mutagenesis libraries that encode many or all single amino acid substitutions in a polypeptide from a protein-coding DNA template sequence. The methods of the invention can involve the simultaneous synthesis of short oligonucleotides that contain all desired variations (e.g., substitutions) on microarrays or other micro-scale solid supports, and then use of these oligonucleotides to construct mutagenesis libraries using multiplexed, seamless cloning reactions. The methods of the invention provide significantly better control over the composition of the DNA library than error-prone PCR, and require significantly less labor and reagents than existing library generation methods (e.g., site-directed mutagenesis).

The invention also provides methods of identifying amino acid residues or nucleic acid sequences that, when mutated, give rise to differences in sensitivity to certain environmental factors. For example, the methods of the invention can be used to determine which mutations in bacteria give rise to sensitivity or resistance to one antibiotic, but do not similarly affect the sensitivity of the bacteria to a second (or further), possibly related antibiotic. In other examples, the methods can be used to determine which mutations in mammalian cells give rise to sensitivity or resistance to a particular drug (e.g., a chemotherapeutic agent), but may not similarly affect the sensitivity of the cells to a second (or further), possibly related drug (e.g., chemotherapeutic agent). The methods of the invention can be adapted to measure differences in sensitivity to environmental factors by detection of a variety of phenotypes. These phenotypes include, for example, growth rate, utilization of certain nutrients, sensitivity to growth or differentiation factors, sensitivity to certain types of mutagenic conditions, expression of marker genes and proteins, and sensitivity to infection by, e.g., viruses.

In brief, these methods of the invention can include providing a diverse library of nucleic acid molecules encoding mutants of a protein or nucleic acid molecule of interest (generated by, e.g., the methods described herein), introducing the library into a cellular population, exposing the cells to at least one environmental factor, isolating cells exhibiting a desired phenotype in response to the at least one environmental factor, and identifying the mutations enriched or depleted in the isolated population as compared to, for example, the starting population of cells or a population of cells incubated in the absence of the environmental factor. In some embodiments, the methods can further include exposing one or more additional populations of cells to a second (or third, etc.) environmental factor, isolating cells exhibiting a desired phenotype, identifying the mutations enriched or depleted in the isolated populations as compared to the mutations present in the starting population and/or enriched in the populations of cells isolated after exposure to the first (or second, etc.) environmental agent. Such comparisons facilitate identification of mutations that confer increased or decreased sensitivity (e.g., selective antibiotic or other drug resistance or sensitivity) to one environmental factor over another.

The Template DNA Molecule

The template DNA molecule is a starting material for the methods of the invention, from which variants of the template DNA molecule are generated. The template DNA molecule can optionally include a sequence that encodes a polypeptide (e.g., a protein), a DNA regulatory element (e.g., a promoter or enhancer), or RNA. The template DNA molecule is typically cloned into a vector, such as a plasmid vector (e.g., a mammalian expression vector, a bacterial expression vector, or a viral vector (e.g., a lentiviral vector), which optionally includes a selectable marker. The template DNA molecule can be 100 nucleotides or more in length (e.g., greater than 100, 150, 200, 300, 500, 1000, 2000, 5000, or 10000 nucleotides in length). In certain embodiments, the template DNA molecule can encode an antibiotic, anti-viral, or chemotherapeutic resistance gene, a protein expressed on a cell surface, or contribute to the regulation of, e.g., a differentiation factor.

The Oligonucleotides

Sets of oligonucleotides used in the invention are typically 100-500 (e.g., 100, 150, 200, 250, 300, 350, 400, 450, or 500) nucleotides in length. Each oligonucleotide may contain zero, one, or more variations (e.g., substitutions, deletions, or insertions) in sequence according to the desired composition of the final mixture of variants. Also, as described elsewhere herein, the oligonucleotides, in some embodiments, can include a central region where sequence variations occur, and invariant 5' and 3' ends, which can be used, for example, as PCR primer recognition sites. The oligonucleotides can thus include, for example, 15-100, 20-80, or 30-50 invariant nucleotides flanking the central region. In one example, the oligonucleotides include 200 nucleotides, with 30 on each end being invariant and flanking a 140 nucleotide central region including variant sequences as described herein.

The oligonucleotides are synthesized using standard methods, e.g., on microarrays (e.g., a programmable microarray) or other micro-scale solid supports. As described further below, in various examples of the invention, a set of long DNA oligonucleotides that encode all desired mutations, but which are otherwise homologous to the template sequence, are designed. The oligonucleotides are organized into 'tiles,' for use in the 'tiling mutagenesis' methods described herein, where those within each tile differ in a central variable region but share identical 5' and 3' ends. The tiles can be staggered such that their variable regions collectively span the entire template. Individual tiles are PCR amplified using primers complementary to their shared ends. To avoid hybridization and extension of partially overlapping oligonucleotides, the tiles can be split into two (or more) non-overlapping pools that are synthesized and amplified separately. PCR products from each tile are inserted into linearized plasmids that carry the remaining template sequence using multiplexed sequence- and ligation-independent cloning.

Method for Construction of Mutagenesis Libraries

Figure 1:
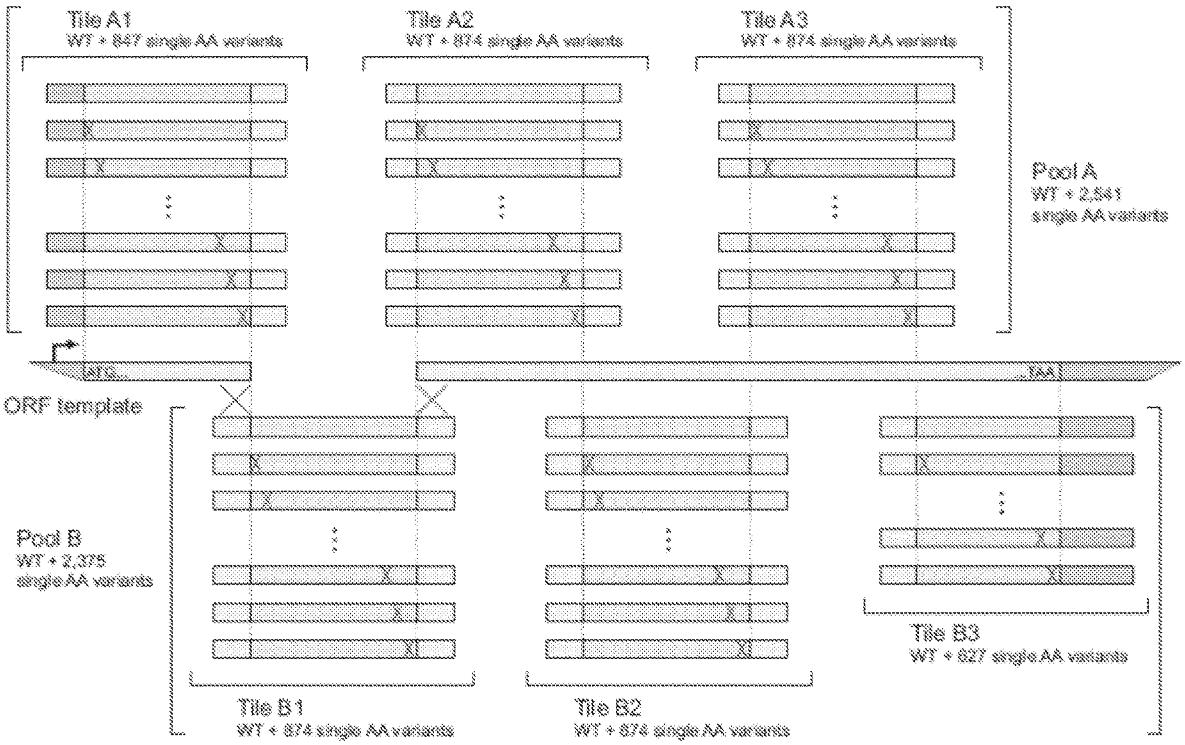
FIG. 1 is a schematic showing an overview of the tiling mutagenesis approach. Oligonucleotides encoding all desired amino acid substitutions in a template open reading frame (ORF) are synthesized in two pools. The oligonucleotides in each pool are organized into non-overlapping tiles with shared 5'- and 3' ends that facilitate selective PCR amplification. After amplification, each tile is inserted into a linearized expression vector that contains the remainder of the ORF using sequence- and ligation-independent cloning techniques.

The methods of the invention are exemplified in the following list of steps:

1) Generating a plasmid vector that contains the template DNA molecule using methods known in the art, including, but not limited to cloning and standard commercial gene synthesis.
2) Designing sets of oligonucleotides, typically 150-250 nucleotides long (e.g., 100, 150, 200, or 250 nucleotides long) as shown in FIG. 1. Each oligonucleotide may contain zero, one, or more variations (e.g., substitutions, deletions, or insertions) in DNA sequence according to the desired composition of the final mixture of variants. Each oligonucleotide may optionally contain either natural or unnatural nucleotides.
3) Synthesizing the designed oligonucleotides, e.g., on microarrays or other micro-scale solid supports. Overlapping oligonucleotides may be separated between two independently synthesized sets as shown in FIG. 1. For improved cost-efficiency, oligonucleotides corresponding to different regions may be synthesized on the same microarray.
4) For each subset of oligonucleotides that corresponds to a region of the template DNA molecule, performing a polymerase chain reaction (PCR) with the oligonucleotide pool using primers homologous to the invariant regions (dark gray in FIG. 1).
5) Preparing a linearized plasmid such that the linear plasmid includes a 5' and a 3' end that can be used to insert the PCR product from step 4 using recombination, ligation, or a combination of these methods. The linearized plasmid vector can be prepared either by performing PCR with the reverse complement primers on the template-containing vector to linearize it. Alternatively, the linearized plasmid vector can be prepared using a restriction enzyme digestion reaction at appropriate DNA sites flanking the region where the variant containing oligonucleotides will be cloned.
6) Purifying the matched linearized plasmid vector and the variant containing oligonucleotides and joining them, e.g., by recombining them in a seamless cloning reaction (e.g., by sequence- and ligation-independent cloning, In-Fusion, Cold Fusion, or Gibson Assembly) to generate a recombinant mixture.
7) Transforming the recombinant mixture from step 6 into propagating cells (e.g., bacterial or yeast cells) and growing cells containing the variant containing circular plasmid using an antibiotic selection (e.g., kanamycin, carabenicillin, ampicillin, or G418) or a nutrient selection (e.g., IPTG-X-gal selection) method known in the art.
8) Repeat steps 4 to 7 for every oligonucleotide region of the template DNA molecule.
9) Isolate plasm ids from the cells that were transformed with each of the sets of variants and combine (e.g., in equimolar ratios) to make the final mixture of variants.

Variants

Sequence variants in the methods of the invention can include substitutions, insertions, or deletions of nucleotides. For example, if a template DNA molecule is an open reading frame that encodes a polypeptide, the methods of the invention can be used to create a mixture of variants in which every amino acid of the polypeptide is changed to at least one (e.g., 2, 3, 4, 5, 6, 10, 15, or 20) of any one of the 20 naturally occurring amino acids or any unnatural amino acids.

If a template DNA molecule encodes a DNA regulatory element (e.g., a transcription factor binding site, an enhancer sequence, or a chromatin remodeling sequence), then the methods of the invention can be used to create a mixture of variants in which every nucleotide of the DNA regulatory element has been changed at least once. Similarly, if the template DNA molecule encodes an RNA molecule (e.g., miRNA, siRNA, or mRNA), then the methods of the invention can be used to create a mixture of variants in which every nucleotide of the encoded RNA has been changed at least once (optionally to all other naturally occurring sequence options and/or to options including unnaturally occurring nucleotides).

The mixture of variants can include plasmids that contain one or more variations in a single region (e.g., 1, 2, 3, 4, 5, 6, 10, 20, 30, 50, 100, or 200 variations) and the mixture may thus include many or all variants of the template DNA molecule. The mixture of variants can include vectors (e.g., plasmids) in which each vector contains one or more variations in different regions corresponding to the template DNA molecule. For example, such a mixture of variants may contain vectors (e.g., plasmids) that represent variations in 1, 2, 3, 10, 15, 20, 100, or 200 regions corresponding to the template DNA molecule.

The mixture of variants can include vectors (e.g., plasmids) that each contain more than one variation in two or more different regions of the template DNA molecule. Such variants can be created by generating a variation in one region first and then using this variant containing vector as an input in the method of the invention for generating further variations in one or more regions.

Alternatively, variation containing oligonucleotides corresponding to two or more overlapping adjacent regions can be joined in a linear manner and then recombined with the linearized plasmid vector to produce a single plasmid containing variations in multiple regions of the template DNA molecule in one step.

Identifying Mutations that Confer Sensitivity to Environmental Factors

The methods of the invention are useful to identify mutations that confer selective sensitivity or resistance of cells to an environmental factor, which can be measured as compared to, for example, cells not exposed to the environmental factor, cells exposed to a second factor, and/or cells exposed to a different concentration or dosage of the first environmental factor. In these methods, the environmental factor can be, e.g., antibiotics, such as antibiotics of the same family. Accordingly, the methods of the invention can be used to determine which mutations provide sensitivity or resistance to one member of an antibiotic family as compared to, for example, a second member of the same family. Such information can be used to inform treatment decisions by identifying whether a particular pathogen infecting a subject contains a mutation that, while providing resistance to a first antibiotic, still provides susceptibility to treatment with a second antibiotic, or to prospectively identify combinations of antibiotics that are not vulnerable to the same resistance mutations, thereby reducing the risk of emergent resistance during the course of treatment.

Antibiotics

As non-limiting examples, the methods of the invention can be used in identifying mutations that confer selective sensitivity or resistance to or between antibiotics selected from among any or all of the following:

Aminoglycosides (e.g., amikacin, gentamicin, kanamycin, neomycin, netilmicin, tobramycin, paromomycin, and apectinomycin).

Ansamycins (e.g., geldanamycin, herbimycin, rifaximin, and streptomycin).

Carbapenems (e.g., ertapenem, doripenem, cilastatin, and meropenem).

First generation cephalosporins (e.g., cefadroxil, cefazolin, cefalotin, and cefalexin).

Second generation cephalosporins (e.g., cefaclor, cefamandole, cefoxitin, cefprozil, and cefuroxime).

Third generation cephalosporins (e.g., cefixime, cefdinir, cefditoren, cefoperazone, cefotaxime, cefpodoxime, ceftazidime, ceftibuten, ceftizoxime, and ceftriaxone).

Fourth and fifth generation cephalosporins (e.g., cefepime, ceftaroline fosamil, and ceftobiprole).

Glycopeptides (e.g., teicoplanin, vancomycin, and telavancin).

Lincosamides (e.g., clindamycin and lincomycin).

Daptomycin.

Macrolides (e.g., azithromycin, clarithromycin, dirithromycin, erythromycin, roxithromycin, troleandomycin, telithromycin, and spiramycin).

Aztreonam.

Nitrofurans (e.g., furazolidone and nitrofurantoin).

Oxazolidonones (e.g., linezolid, posizolid, radezolid, and torezolid).

Penicillins (amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, and ticarcillin).

Penicillin combinations (e.g., amoxicillin/clavulanate, ampicillin/sulbactam, piperacillin/tazobactam, and ticarcillin/clavulanate).

Polypeptides (e.g., bacitracin, colistin, and polymyxin B).

Quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin).

Sulfonamides (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole, and sulfonamidochrysoidine).

Tetracyclines (e.g., demeclocycline, doxycycline, minocycline, oxytetracycline, and tetracycline).

Chemotherapeutic Agents

As further non-limiting examples, the methods of the invention are useful in identifying mutations that confer selective sensitivity or resistance to or between chemotherapeutic agents selected from among any or all of the following:

Alkylating agent (e.g., cyclophosphamide, mechlorethamine, chlorambucil, and melphalan).

Anthracyclines (e.g., daunorubicin, doxorubicin, epirubicin, idarubicin, mitoxantrone, and valrubicin).

Cytoskeletal disruptors (taxanes) (e.g., paclitaxel, and docetaxel).

Epothilones.

Histone deacetylase inhibitors (e.g., vorinostat and romidepsin).

Inhibitors of topoisomerase I (e.g., irinotecan and topotecan).

Inhibitors of topoisomerase II (e.g., etoposide, teniposide, and tafluposide).

Kinase inhibitors (e.g., bortezomib, erlotinib, gefitinib, imatinib, vemurafenib, and vismodegib).

Monoclonal antibodies (e.g., bevacizumab, cetuximab, ipilimumab, ofatumumab, ocrelizumab, panitumab, and rituximab).

Nucleotide analogs and precursor analogs (e.g., azacitidine, azathioprine, capecitabine, cytarabine, doxifluridine, fluorouracil, gemcitabine, hydroxyurea, mercaptopurine, methotrexate, and tioguanine (formerly thioguanine).

Peptide antibiotics (e.g., bleomycin and actinomycin).

Platinum-based agents (e.g., carboplatin, cisplatin, and oxaliplatin).

Retinoids (e.g., tretinoin, alitretinoin, and bexarotene).

Vinca alkaloids and derivatives (e.g., vinblastine, vincristine, vindesine, and vinorelbine).

Anti-Viral Agents

As further non-limiting examples, the methods of the invention are useful in identifying mutations that confer selective sensitivity or resistance to or between anti-viral agents selected, e.g., from among any or all of the following:

Abacavir, aciclovir, acyclovir, adefovir, amantadine, amprenavir, ampligen, arbidol, atazanavir, atripla (fixed dose drug), balavir, boceprevirertet, cidofovir, combivir (fixed dose drug), darunavir, delavirdine, didanosine, docosanol, edoxudine, efavirenz, emtricitabine, enfuvirtide, entecavir, entry inhibitors, famciclovir, fixed dose combination (antiretroviral), fomivirsen, fosamprenavir, foscarnet, fosfonet, fusion inhibitor, ganciclovir, ibacitabine, imunovir, idoxuridine, imiquimod, indinavir, inosine, integrase inhibitor, interferon type iii, interferon type ii, interferon type i, interferon, lamivudine, lopinavir, loviride, maraviroc, moroxydine, methisazone, nelfinavir, nevirapine, nexavir, nucleoside analogues, oseltamivir, peginterferon alfa-2a, penciclovir, peramivir, pleconaril, podophyllotoxin, protease inhibitor (pharmacology), raltegravir, reverse transcriptase inhibitor, ribavirin, rimantadine, ritonavir, pyramidine, saquinavir, stavudine, synergistic enhancer (antiretroviral), tea tree oil, telaprevir, tenofovir, tenofovir disoproxil, tipranavir, trifluridine, trizivir, tromantadine, truvada, valaciclovir (valtrex), valganciclovir, vicriviroc, vidarabine, viramidine, zalcitabine, zanamivir, and zidovudine.

Anti-Fungal Agents

As further non-limiting examples, the methods of the invention are useful in identifying mutations that confer selective sensitivity or resistance between anti-fungal agents selected, e.g., from among any or all of the following:

Polyene antifungals (e.g., Amphotericin b, candicidin, filipin, hamycin, natamycin, nystatin, and rimocidin).

Imidazoles (e.g., Bifonazole, butoconazole, clotrimazole, econazole, fenticonazole, isoconazole, ketoconazole, miconazole, omoconazole, oxiconazole, sertaconazole, sulconazole, and tioconazole).

Triazoles (e.g., Albaconazole, fluconazole, isavuconazole, itraconazole, posaconazole, ravuconazole, terconazole, and voriconazole).

Thiazoles (e.g., Abafungin).

Allylamines (e.g., Amorolfin, butenafine, naftifine, and terbinafine).

Echinocandins (e.g., Anidulafungin, caspofungin, and micafungin).

Others (e.g., Benzoic acid, ciclopirox, flucytosine or 5-fluorocytosine, griseofulvin, haloprogin, polygodial, tolnaftate, undecylenic acid, and crystal violet).

Alternatives (e.g., oregano, allicin, citronella oil, coconut oil, iodine—lugol's iodine, lemon myrtle, neem seed oil, olive leaf, orange oil, palmarosa oil, patchouli, selenium, tea tree oil—iso 4730 ("oil of melaleuca, terpinen-4-ol type"), zinc, and horopito (pseudowintera colorata) leaf contains the antifungal compound polygodial, turnip, chives, radish).

Pathogenic Organisms

As further non-limiting examples, the methods of the invention are useful in identifying mutations that confer selective sensitivity or resistance to pathogenic organisms (or toxins or components of such organisms or particles that mediate cell entry or other interactions with the host cell, etc). In other examples, the methods of the invention are useful in identifying mutations in pathogenic organisms that make them more or less sensitive to antibiotic agents or more or less toxic to cells. Pathogenic organisms are selected, e.g., from among any or all of the following:

*Bordetella* (e.g., *Bordetella pertussis*), *borrelia* (e.g., *Borrelia burgdorferi*), *brucella* (e.g., *brucella abortus, brucella canis, brucella melitensis, brucella suis*), *campylobacter* (e.g., *Campylobacter jejuni*), *chlamydia* and *chlamydophila* (e.g., *Chlamydia pneumoniae, Chlamydia trachomatis, chlamydophila psittaci*), *clostridium* (e.g., *Clostridium botulinum, Clostridium difficile, Clostridium perfringens, Clostridium tetani*), *corynebacterium* (e.g., *Corynebacterium diphtheriae*), *enterococcus* (e.g., *Enterococcus faecalis, Enterococcus faecium*), *escherichia* (e.g., *Escherichia coli*), *francisella* (e.g., *Francisella tularensis*), *haemophilus* (e.g., *Haemophilus influenzae*), *helicobacter* (e.g., *Helicobacter pylori*), *legionella* (e.g., *Legionella pneumophila*), *leptospira* (e.g., *leptospira interrogans*), *listeria* (e.g., *Listeria monocytogenes*), *mycobacterium* (e.g., *Mycobacterium leprae, Mycobacterium tuberculosis, Mycobacterium ulcerans*), *mycoplasma* (e.g., *Mycoplasma pneumoniae*), *neisseria* (e.g., *Neisseria gonorrhoeae, Neisseria meningitidis*), *pseudomonas* (e.g., *Pseudomonas aeruginosa*), *rickettsia* (e.g., *Rickettsia rickettsii*), *salmonella* (e.g., *Salmonella typhi, Salmonella typhimurium*), *shigella* (e.g., *Shigella sonnei*), *staphylococcus* (e.g., *Staphylococcus aureus, Staphylococcus epidermidis, Staphylococcus saprophyticus*), *streptococcus* (e.g., *Streptococcus agalactiae, Streptococcus pneumoniae, Streptococcus pyogenes*), *treponema* (e.g., *Treponema pallidum*), *vibrio* (e.g., *Vibrio cholerae*), and *yersinia* (e.g., *Yersinia pestis*).

Hormones

As further non-limiting examples, the methods of the invention are useful in identifying mutations that change the sensitivity or resistance of cells to certain hormones or groups of hormones, e.g., from among any or all of the following hormones:

Eicosanoid (e.g., prostaglandins, leukotrienes, prostacyclin, and thromboxane).

Peptide (e.g., Amylin (or islet amyloid polypeptide), antimullerian hormone (or müllerian inhibiting factor or hormone), adiponectin, adrenocorticotropic hormone (or corticotropin), angiotensinogen and angiotensin, antidiuretic hormone (or vasopressin, arginine vasopressin), atrial-natriuretic peptide (or atriopeptin), brain natriuretic peptide, calcitonin, cholecystokinin, corticotropin-releasing hormone, enkephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, insulin-like growth factor (or somatomedin), leptin, lipotropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostatin, thrombopoietin, thyroid-stimulating hormone (or thyrotropin), and thyrotropin-releasing hormone).

Steroid (e.g., Testosterone, dehydroepiandrosterone, androstenedione, dihydrotestosterone, aldosterone, estradiol, estrone, estriol, cortisol, progesterone, calcitriol (1,25-dihydroxyvitamin d3), and calcidiol (25-hydroxyvitamin d3)).

Anti-Inflammatory Agents

As further non-limiting examples, the methods of the invention are useful in identifying mutations that change the sensitivity of cells to certain anti-inflammatory agents, e.g., from among any or all of the following hormones:

Salicylates (e.g., aspirin (acetylsalicylic acid), diflunisal, and salsalate)

Propionic acid derivatives (e.g., Ibuprofen, dexibuprofen, naproxen, fenoprofen, ketoprofen, dexketoprofen, flurbiprofen, oxaprozin, and loxoprofen).

Acetic acid derivatives (e.g., Indomethacin, tolmetin, sulindac, etodolac, ketorolac, diclofenac, and nabumetone).

Enolic acid (oxicam) derivatives (e.g., Piroxicam, meloxicam, tenoxicam, droxicam, lornoxicam, and isoxicam).

Fenamic acid derivatives (fenamates) (e.g., Mefenamic acid, meclofenamic acid, flufenamic acid, and tolfenamic acid).

Selective cox-2 inhibitors (coxibs) (e.g., Celecoxib, rofecoxib, valdecoxib, parecoxib, lumiracoxib, etoricoxib, firocoxib, and paracetamol).

Sulphonanilides (e.g., Nimesulide).

Others (e.g., Licofelone and lysine clonixinate).

Natural (e.g., Hyperforin, figwort, and calcitriol (vitamin d)).

Corticosteroids (e.g. corticosterone, deoxycorticosterone, cortisol, 11-deoxycortisol, cortisone, 18-hydroxycorticosterone, 1α-hydroxycorticosterone, and aldosterone).

In other embodiments, the environmental factors used in the methods of the invention can be, e.g., growth factors, drugs, nutrients (e.g., carbon sources, vitamins, etc.), cellular toxins, anti-aging compounds, anti-protozoan compounds, differentiation factors, mutagens (e.g., ultraviolet light, X-rays, gamma rays, and chemical carcinogens), temperature, pressure, pH, salinity, and viscosity.

In other embodiments, the environmental factors used in the methods of the invention can be pathogenic organisms or particles that attach to or enter cells, including viral particles (e.g., adenovirus, picornavirus, herpesvirus, flavivirus, polyomavirus, retrovirus, rhabdovirus and togavirus) and components of such organisms or particles that mediate cell entry or other interactions with the host cell (e.g., virion enveloped glycoproteins such as HIV gp120 and Herpes simplex virus gC and gD).

The methods of isolating cells exposed to a particular environmental factor will depend on the nature of the environmental factor. If, for example, the environmental factor affects the growth rate of the cell or results in cell death, cells can be isolated by selection methods. In this embodiment, for example, if the variant increases sensitivity to the an environmental factor resulting in decreased growth rate or is toxic to a cell population, or decreases sensitivity to a factor that increases the growth rate of a cell, that variant would be depleted upon exposure to that environmental factor. If the variant increases sensitivity to a factor that promotes growth of the cell, or if the variant decreases sensitivity to an environmental factor decreases the growth rate or is toxic to the cell, then that variant will be enriched in the resulting cell population. If, for example, the environmental factor affects morphological aspects of the cell (e.g., expression of differentiation factors or other markers, cell size, cell wall integrity, cellular adhesion, cell cycle arrest, or secretion of certain factors (e.g., inflammatory factors), cells can be isolated on the basis of their morphology (e.g., by fluorescent activated cell sorting) or expression patterns, and variants enriched in the isolated cell population can be subsequently identified.

Once isolated, mutations giving rise to differing sensitivities or resistance to environmental agents can be identified, e.g., by sequence analysis or hybridization analysis. In performing sequence analysis, the entire variant nucleic acid can be sequenced (e.g., from a set of primers universal to the variant nucleic acid sequence), a portion of the variant can be sequenced (e.g., the portion corresponding to a nucleic acid tag), or the entire nucleic acid content of the cell can be sequences (e.g., using next generation sequencing techniques).

EXPERIMENTAL RESULTS

Sensitivity to Related Antibiotics

To enable efficient generation of relatively unbiased, single amino acid substitution libraries, we developed a highly multiplexed approach to site-directed mutagenesis that we refer to as tiling mutagenesis (FIG. 1). We designed a set of long DNA oligonucleotides that encode all desired mutations, but are otherwise homologous to the template sequence. The oligonucleotides are organized into 'tiles', where those within each tile differ in a central variable region but share identical 5' and 3' ends. The tiles are staggered such that their variable regions collectively span the entire template. The oligonucleotides are synthesized on a programmable microarray (LeProust, E. M. et al. Synthesis of high-quality libraries of long (150 mer) oligonucleotides by a novel depurination controlled process. *Nucleic acids research* 38, 2522-40 (2010)) and individual tiles are then PCR amplified using primers complementary to their shared ends. To avoid hybridization and extension of partially overlapping oligonucleotides, the tiles can be split into two non-overlapping pools that are synthesized and amplified separately. Finally, the PCR products from each tile are inserted into linearized plasmids that carry the remaining template sequence using multiplexed sequence- and ligation-independent cloning. Because only a portion of each resulting mutant sequence is derived from the oligonucleotide pool, this approach limits the impact of synthesis errors but still benefits from the cost efficiency of microarray-based DNA synthesis.

We applied the methods to perform mutational scanning of the Tn5 transposon-derived aminoglycoside-3'-phosphotransferase-II (APH(3')II), a 264 amino acid residues kinase that confers resistance to a variety of aminoglycoside antibiotics (Nurizzo, D. et al. The Crystal Structure of Aminoglycoside-3'-Phosphotransferase-IIa, an Enzyme Responsible for Antibiotic Resistance. *Journal of Molecular Biology* 327, 491-506 (2003)), with the goal of elucidating which residues are essential for its activity and whether these residues are the same for different substrates. We first designed and synthesized six 200 nucleotide (nt) tiles that encoded all possible single amino acid substitutions across APH(3')II. Each tile contained a 140 nt variable region flanked by 30 nt constant ends. To test whether the cost-efficiency of our method could be further improved by synthesizing multiple mutant libraries in parallel, we also included corresponding tiles for nine homologous proteins, resulting in two non-overlapping pools of 26,250 and 23,666 distinct oligonucleotide sequences. We found that all six APH(3')II tiles could be selectively amplified from these pools with minimal optimization of PCR conditions. We then inserted these tiles into plasmids that carried the corresponding remainders of the APH(3')II coding sequence. Each amplification and multiplexed cloning reaction was performed in duplicate to generate two mutant libraries.

Figure 2:
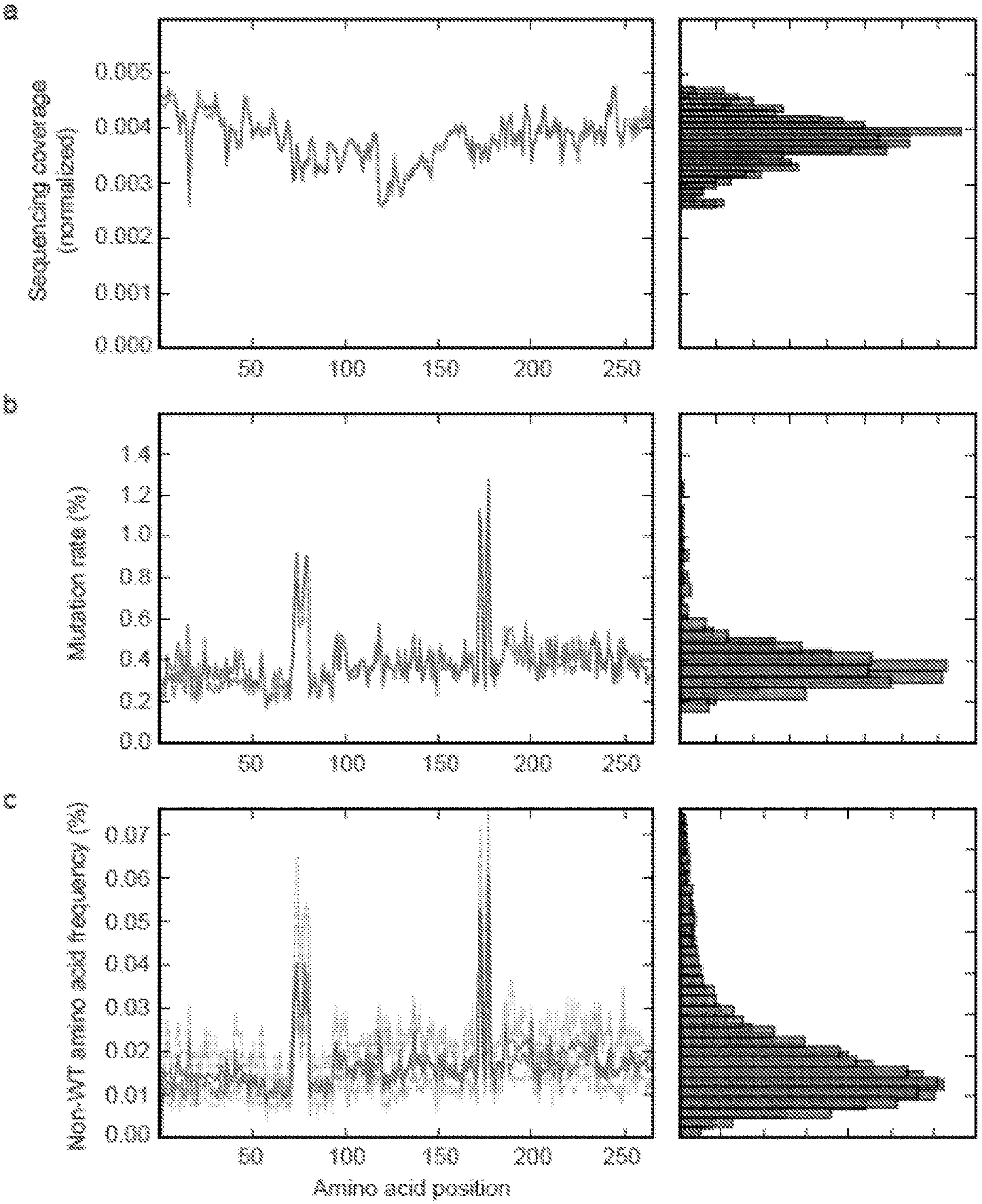
FIG. 2 is a series of graphs showing sequencing-based quality control of the APH('3)II mutant libraries prior to selection. Two libraries were independently constructed from the same raw oligonucleotide synthesis products. (a) High-quality sequence coverage across the APH(3')II coding region, as represented by the number of observations of each codon with phred quality scores ≥30 at all three positions (normalized by division by the median raw count). The observed variation is likely caused by insertional bias of the Nextera transposons. (b) Mutation rate (# of non-WT amino acids/# of amino acids observed per position). Two hotspots appear to trace back to overrepresentation of a subset of oligonucleotides in the raw synthesis product, but their effects on the overall library composition are limited. (c) Frequencies of each non-WT amino acid (# of one amino acid/# of all amino acids) at each position. The dark lines in the left-hand side plot show the median and the light lines show the 1st and 3rd quartiles at each position. The right-hand side histograms show the complete distribution (n=4,997).

To characterize the resulting libraries, we first shotgun-sequenced their APH(3')II coding regions to a depth of ~120,000× (FIG. 2). At this depth, we could detect 4,993 of 4,997 possible substitutions and found that the frequency of each mutant amino acid at each position was close to the expected value from an ideal single substitution library (observed median=0.016%, interquartile range=0.011%-0.023%, expected=0.020%). Amino acid mutations caused by single nucleotide substitutions were slightly overrepresented, which is likely due to the combined effects of synthesis- and sequencing-related errors. We next subcloned 90 plasmids from the libraries for full-length sequencing of the coding region and found that the majority (90%) of these clones carried a single amino acid substitution, while the rest carried either none (2.2%) or two substitutions (7.8%). We also found that ~30% of the clones carried small (1-4 nt) deletions within the oligonucleotide-derived regions. To minimize the impact of these potentially inactivating deletions, each library was generated to contain plasmids from ~$10^7$ transformants. This ensured that the majority of plasmids that carried any given substitution were error free, because they would largely be derived from different molecules in the original synthetic pool. Frameshift counter-selection could be used to further clean the libraries (Zacchi, P., Sblattero, D. & Florian, F. Selecting open reading frames from DNA. *Genome Research* 13, 980-990 (2003)), but this was not necessary to obtain the results we describe below.

Figure 3:
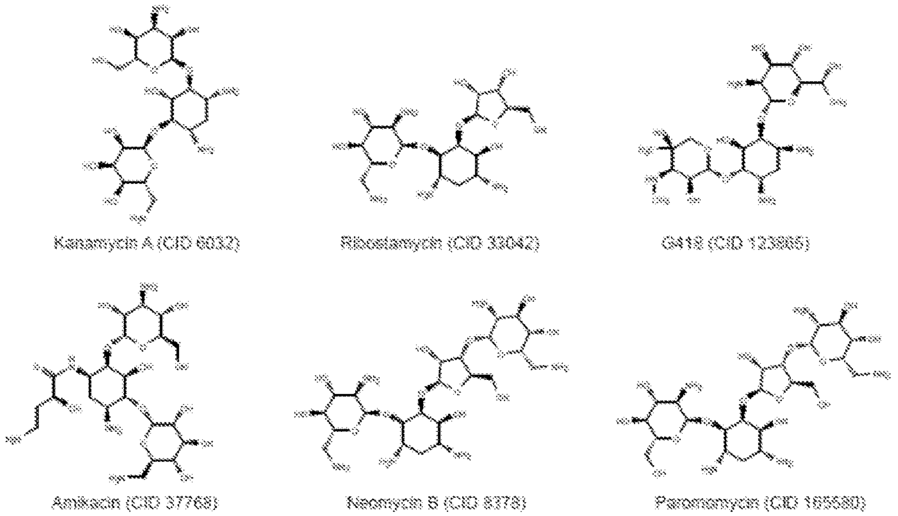
FIG. 3*a* is a series of chemical formulas showing 2-dimensional structures of the six aminoglycoside antibiotics used for selection in this study. The structures were obtained from PubChem (pubchem.ncbi.nlm.nih.gov/) and rendered using Open Babel (openbabel.org/).
FIG. 3*b* is a graph showing optical density (600 nm) in cultures of *E. coli* transformed with WT pBR322[EM7-neo] after 24 hours in liquid LB supplemented with the indicated antibiotic concentrations and 50 μg/mL carbencillin. The potency of the six compounds, as estimated by their minimum inhibitory concentrations (MICs), differ by three orders of magnitude.
Figure 3:
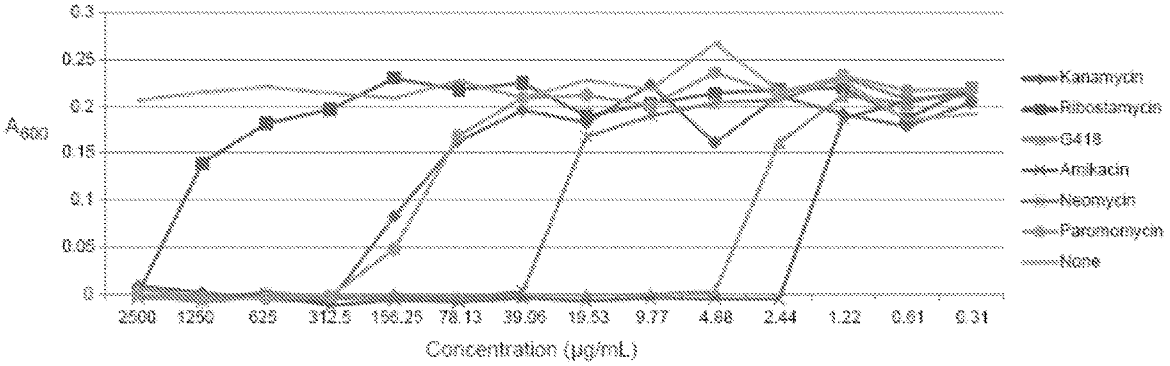

To perform mutational scanning in vivo, we cultured *E. coli* transformed with APH(3')II substitution libraries in liquid media supplemented with decreasing concentrations of one of six aminoglycoside antibiotics with diverse structures and a wide range of potencies: kanamycin, ribostamycin, G418, amikacin, neomycin or paromomycin (FIG. 3). To normalize the selective pressures induced by the different antibiotics, we first established their minimum inhibitory concentrations (MICs) for *E. coli* transformed with "wild-type" (WT) APH(3')II and then used 1:1, 1:2, 1:4 and 1:8 dilutions of WT MICs for the respective library selections. We note that, with the exception of G418 and amikacin, even the 1:8 dilutions were sufficient to inhibit growth of untransformed *E. coli*. After overnight selection, plasmids were isolated from the surviving cells and their coding regions were shotgun sequenced to compare the amino acid composition of the selected libraries to that of the original input libraries (median coverage=51,400×).

Figure 4:
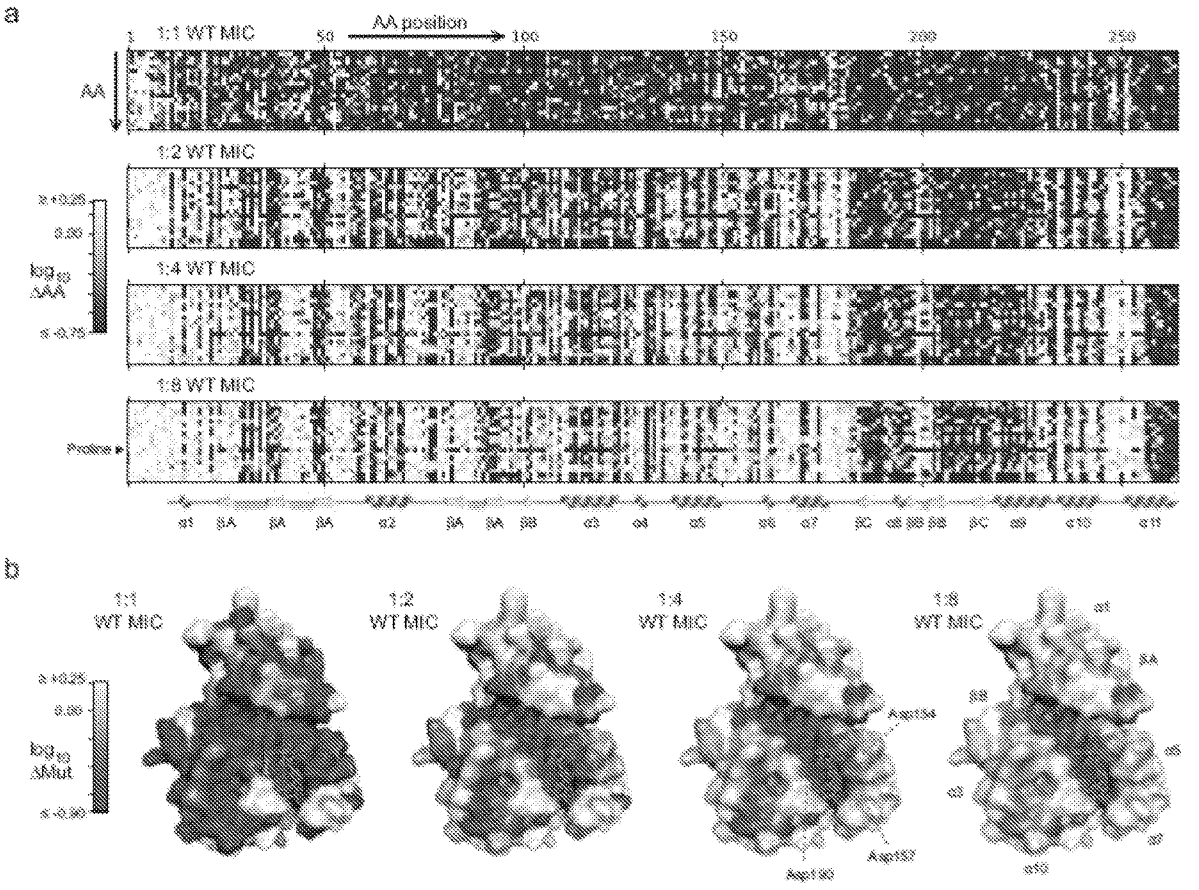
FIG. 4 is a graph showing mutational scanning of APH (3')II using kanamycin selection. (a) Visual representation of the changes in abundance of each amino acid (ΔAA) at each position after selection at four different concentrations. The shading in each matrix entry corresponds to the change relative to the input library. The known secondary structure of APH(3')II is shown for reference, including alpha helices, beta sheet strands, and beta hairpins (the first 10 residues are unstructured). The highly deleterious effect of proline substitutions, which impose unique structural constrains, stand out at low concentrations. (b) Projections of the observed changes in the abundance of mutant amino acids (ΔMut) onto a crystal structure of APH('3)II in complex with kanamycin (PDB accession: 1ND4).
Figure 5:
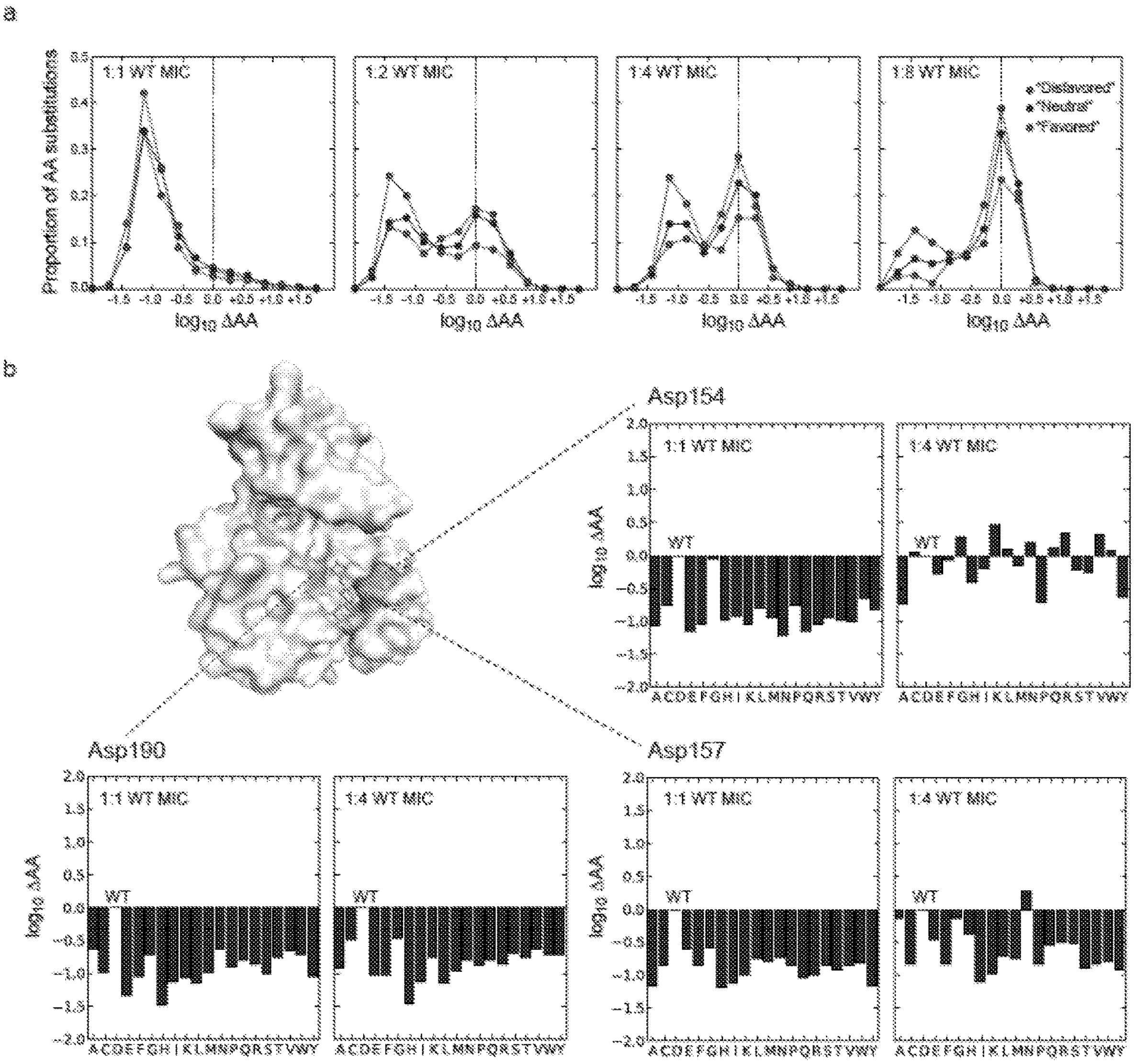
FIG. 5*a* is a series of graphs showing distributions of changes in amino acid frequencies (ΔAA) at each position after selection with kanamycin at four concentrations. The amino acids are divided into three classes, according to whether they would be considered a "disfavored", "neutral" or "favored" substitution from the WT residue in an intracellular protein purely based on their biochemical properties (as estimated by Russell et al, www.russelllab.org/aas/, accessed April 2013). A greater diversity of substitutions were tolerated at low concentrations, although the ratio of "favored" over "disfavored" substitutions that were well-tolerated (log 10 ΔAA≥0.0) was relatively constant at ~1.4.
FIG. 5*b* is an image of a crystal structure and a series of graphs showing examples of concentration- and position-dependent selection patterns for three positions containing aspartate residues in the WT APH(3')II protein. The bar plots show the changes in the observed frequency of each amino acid after selection at the indicated concentrations. Asp190 is believed to be the primary catalytic residue in APH(3')II, while Asp157 contributes a hydrogen bond in the APH(3')II-kanamycin co-crystal.
Figure 6:
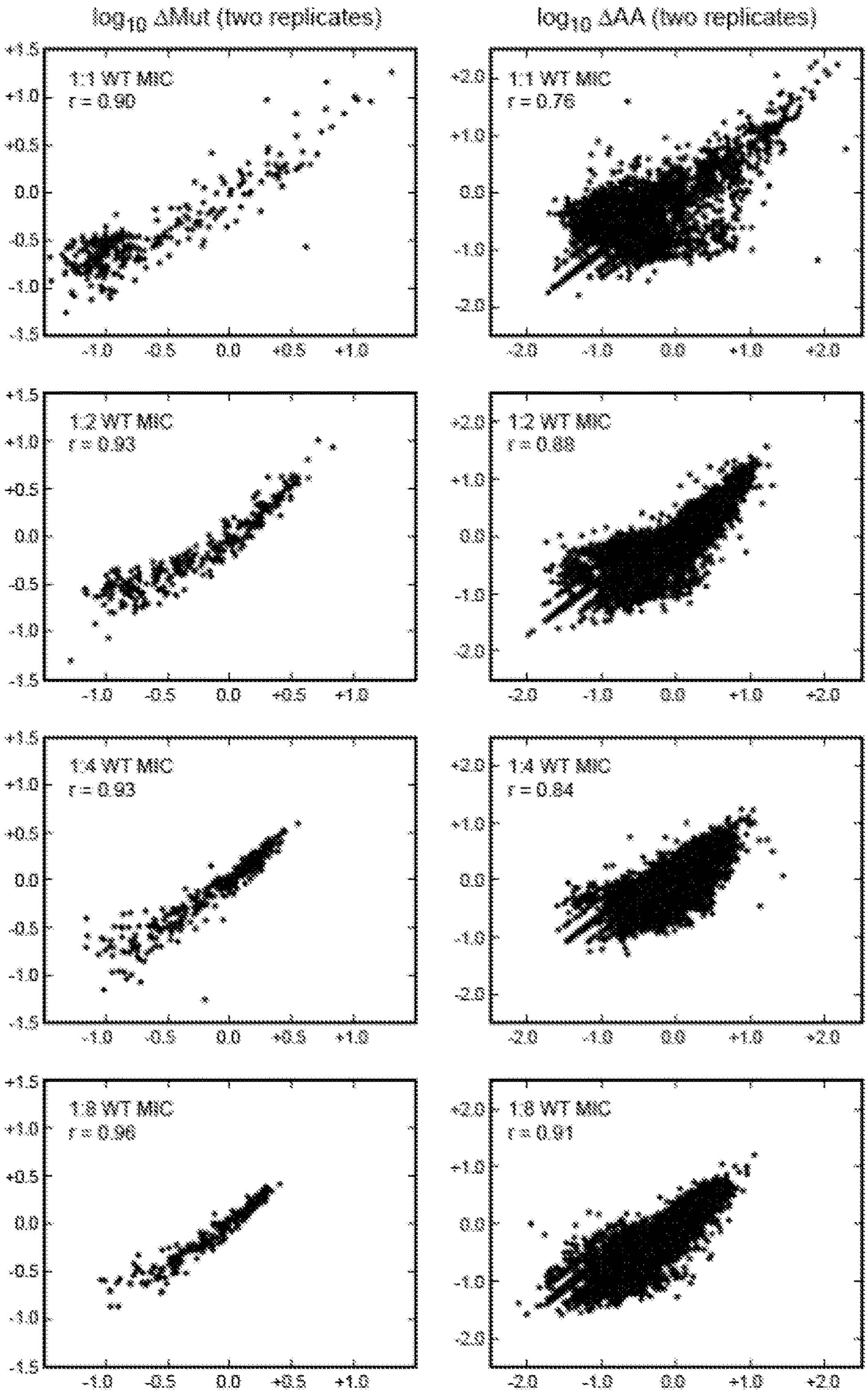
FIG. 6 is a series of scatter plots of the observed changes in the frequencies of mutant amino acids (left) or individual amino acids (right) in two independent kanamycin selection experiments at the indicated concentrations. The Pearson correlation coefficients (r) are all significant at $p<10^{-20}$.

We began our analysis by examining changes in the relative abundance of mutant versus WT amino acids at each position after selection with kanamycin (FIG. 4*a*). At the highest concentration (1:1 WT MIC), we observed a significant depletion of mutant amino acids at approximately 210 of 263 positions ($\chi^2$-test at the 5% false discovery rate (FDR) threshold, as determined by the Benjamini-Hochberg procedure (Benjamini, Y. & Hochberg, Y. Controlling the false discovery rate: a practical and powerful approach to multiple testing. *Journal of the Royal Statistical Society. Series B.* 57, 289-300 (1995))). At lower concentrations, we observed both a decrease in the number of positions with significant depletion of mutations (approximately 155, 130 and 113 at 1:2, 1:4 and 1:8 WT MIC, respectively; 5% FDR) and an increase in the diversity of amino acids that were tolerated at the remaining positions. Conservative substitutions to amino acids with biochemical properties that were similar to the WT residue were on average ~1.4-fold more likely to be tolerated compared to non-conservative substitutions (Betts, M. J. & Russell, R. B. Amino acid properties and consequences of substitutions. *Bioinformatics for Geneticists* 218-316 (2003)), regardless of the kanamycin concentration (FIG. 5*a*). The tolerance for specific substitutions appeared, however, to be both concentration- and position-dependent. Importantly, the observed changes in amino acid frequencies were highly consistent between independent selections (Pearson's r=0.76-0.91 across the four kanamycin dilutions; FIG. 6).

To better understand the patterns of selection, we projected them onto a crystal structure of APH(3')II in complex with kanamycin (Nurizzo, D. et al. The Crystal Structure of Aminoglycoside-3'-Phosphotransferase-IIa, an Enzyme Responsible for Antibiotic Resistance. *Journal of Molecular Biology* 327, 491-506 (2003)) (FIG. 4*b*). These projections show that while mutations are depleted from positions all over the protein at high concentrations, the positions that do not tolerate mutations even at low concentrations tend to cluster internally and near the active site of the enzyme. The projections also provide insights into selection patterns at specific positions. For example, residues 190, 157 and 154 are all aspartates in the vicinity of the active site in the WT enzyme (FIG. 5*b*). At 1:1 WT MIC, we observed depletion of all amino acids except the wild-type aspartates at 190 and 157, while both aspartate and glycine were tolerated at 154. At more moderate selection pressures (1:4 WT MIC), aspartate remained the only amino acid tolerated at 190, aspartate and asparagine were both tolerated at 157, while a wide variety of amino acids, including glycine, valine and arginine, were tolerated at 154. Consistent with its apparent immutability, structural and functional studies have previously identified Asp190 as the catalytic residue in APH(3')II and it is conserved across all known aminoglycoside phosphotransferases (Nurizzo, D. et al. The Crystal Structure of Aminoglycoside-3'-Phosphotransferase-IIa, an Enzyme Responsible for Antibiotic Resistance. *Journal of Molecular Biology* 327, 491-506 (2003)). The crystal structure also shows that Asp157 forms a stabilizing hydrogen bond with the second ring of kanamycin, which explains why substitutions to amino acids other than the very similar asparginine might be deleterious. In contrast, Asp154 does not appear to directly interact with the substrate, which is consistent with the higher tolerance we observed for non-conservative substitutions at this position.

Figure 7:
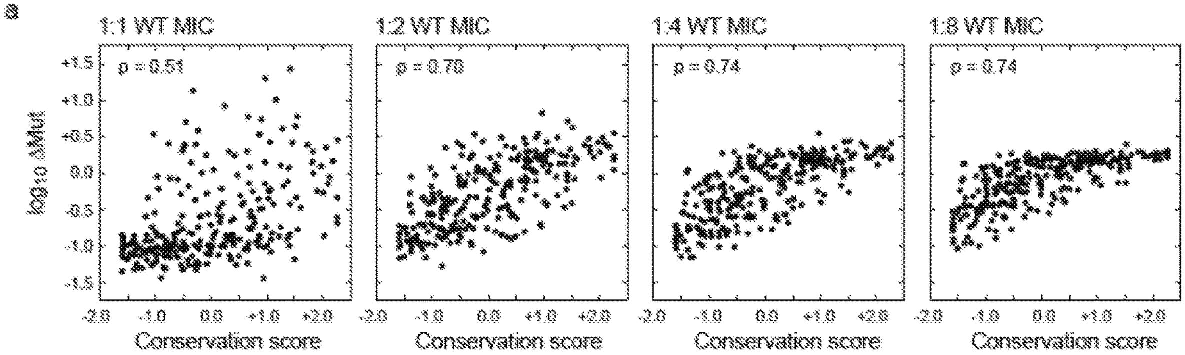
FIG. 7*a* is a series of scatter plots and Spearman's rank correlation coefficients comparing the level of evolutionary conservation at each position along APH(3')II to the observed changes in the frequencies of mutant amino acids under selection with kanamycin at the indicated concentrations. The conservation scores were obtained for the from ConSurf-DB (bental.tau.ac.il/new_ConSurfDB/, accession 1ND4, April 2013).
FIG. 7*b* is an image of a crystal structure and table showing enumeration of the positions that show relatively strong evolutionary conservation (conservation score<0.0), but also high tolerances for one or more non-WT substitutions (log 10 ΔMut>0.0) under selection with kanamycin at 1:1 WT MIC across two replicates.
Figure 7:
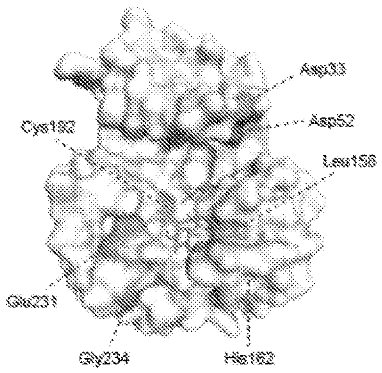
Figure 8:
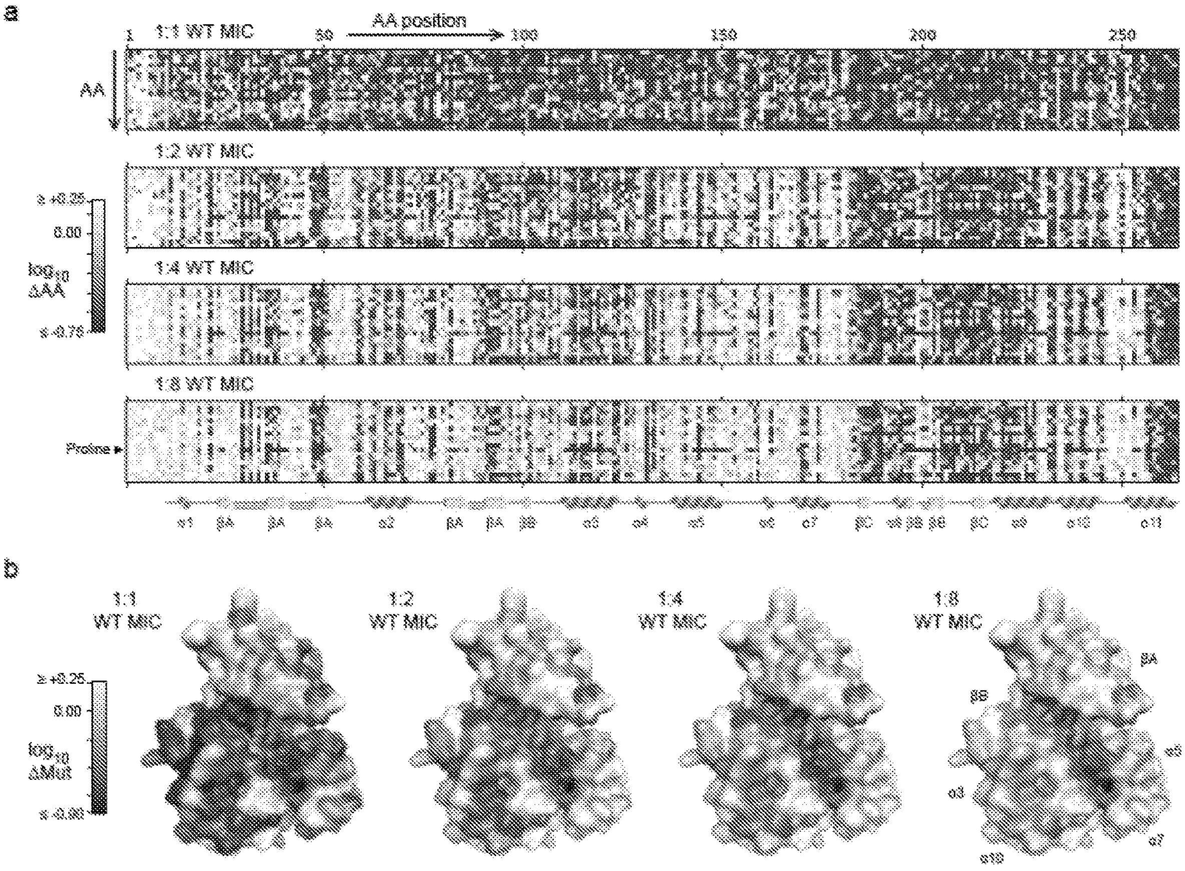
FIG. 8 shows mutational scanning of APH(3')II using ribostamycin selection. (a) is a series of graphs showing a visual representation of the abundance of each amino acid (ΔAA) at each position after selection at four different concentrations. The shading in each matrix entry corresponds to the change relative to the input library. The known secondary structure of APH(3')II is shown for reference, including alpha helices, beta sheet strands and beta hairpins (the first 10 residues are unstructured). (b) is a series of projections of the observed changes in the abundance of mutant amino acids (ΔMut) onto a crystal structure of APH('3)II in complex with kanamycin (PDB accession: 1ND4; the kanamycin substrate is not show).
Figure 9:
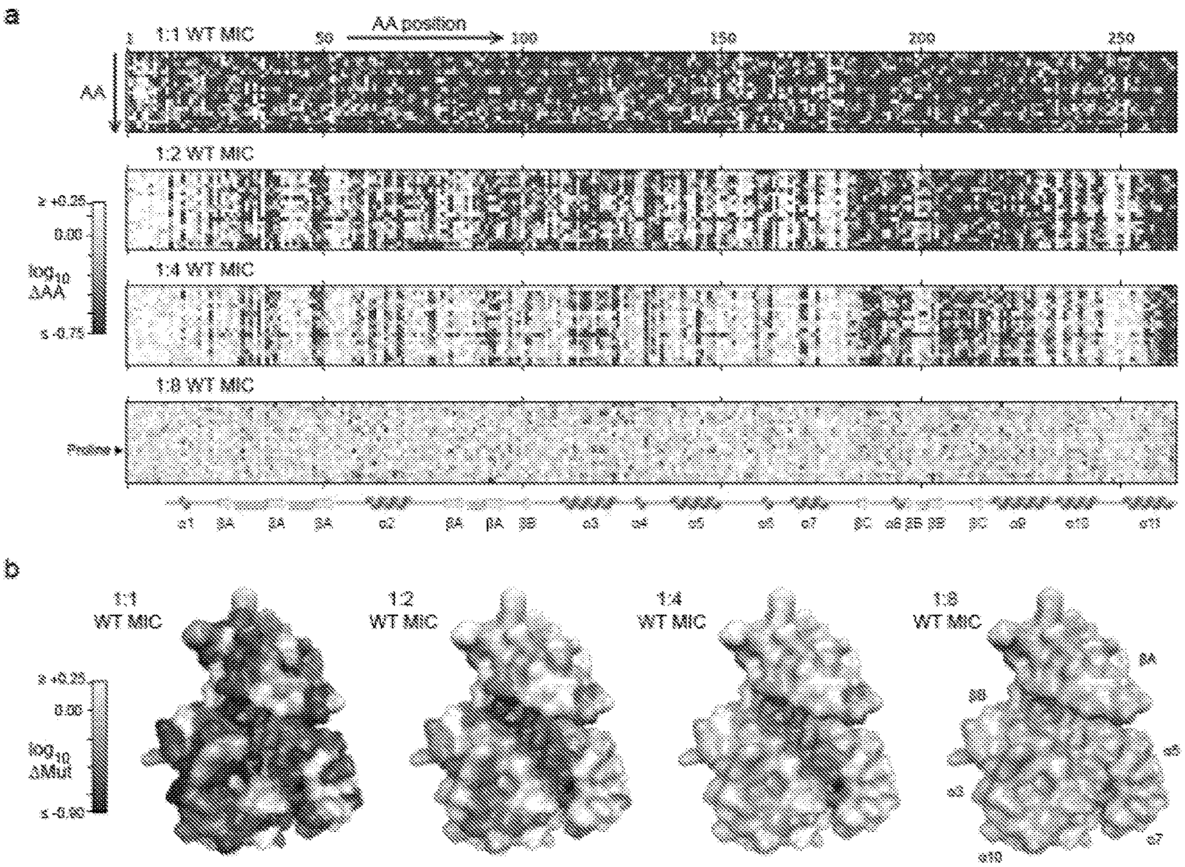
FIG. 9 shows mutational scanning of APH(3')II using G418 selection. (a) is a series of graphs showing a visual representation of the abundance of each amino acid (ΔAA) at each position after selection at four different concentrations. The shading in each matrix entry corresponds to the change relative to the input library. The known secondary structure of APH(3')II is shown for reference, including alpha helices, beta sheet strands, and beta hairpins (the first 10 residues are unstructured). Note that G418 did not provide an effective selection pressure at its 1:8 WT MIC. (b) is a series of projections of the observed changes in the abundance of mutant amino acids (ΔMut) onto a crystal structure of APH('3)II in complex with kanamycin (PDB accession: 1ND4; the kanamycin substrate is not show).
Figure 10:
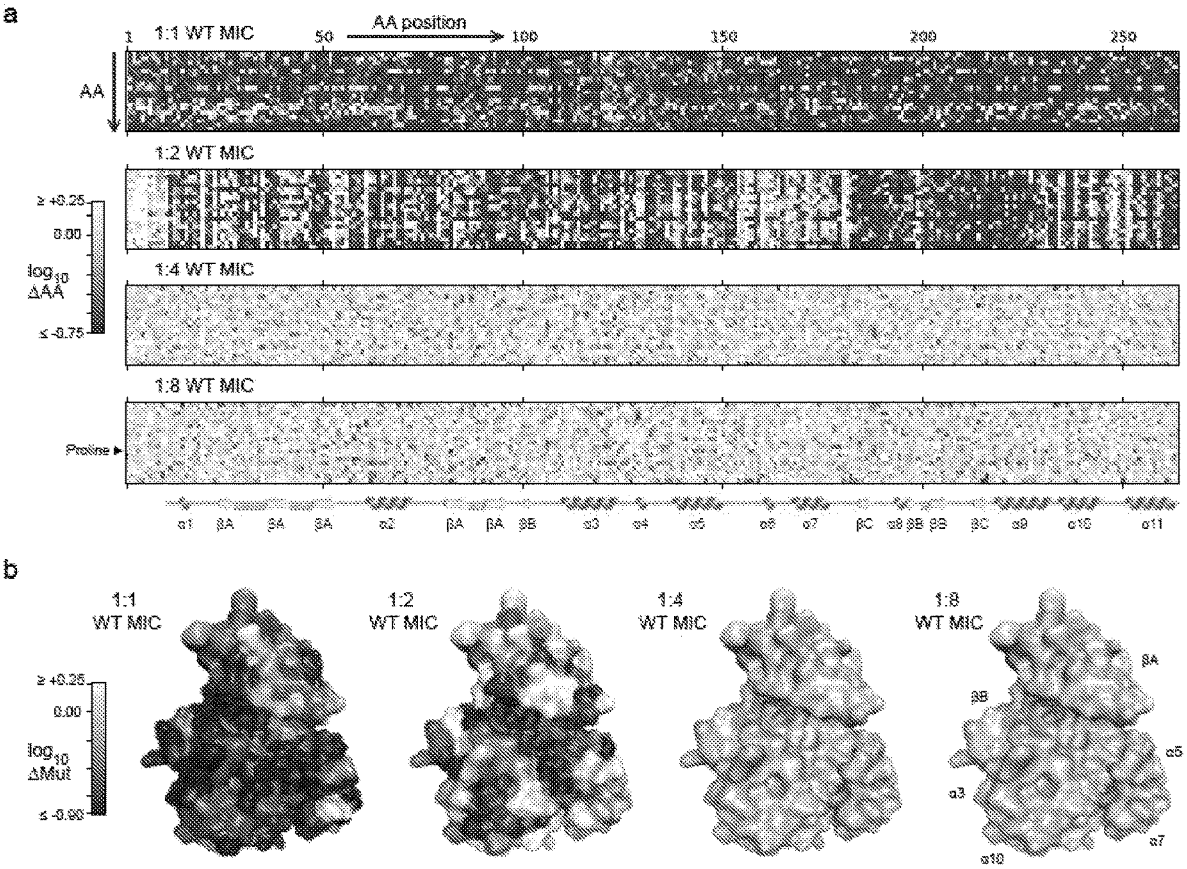
FIG. 10 shows mutational scanning of APH(3')II using amikacin selection. (a) is a series of graphs showing a visual representation of the abundance of each amino acid (ΔAA) at each position after selection at four different concentrations. The shading in each matrix entry corresponds to the change relative to the input library. The known secondary structure of APH(3')II is shown for reference, including alpha helices, beta sheet strands, and beta hairpins (the first 10 residues are unstructured). Note that amikacin did not provide an effective selection pressure at its 1:4 and 1:8 WT MICs. (b) is a series of projections of the observed changes in the abundance of mutant amino acids (ΔMut) onto a crystal structure of APH('3)II in complex with kanamycin (PDB accession: 1ND4; the kanamycin substrate is not show).
Figure 11:
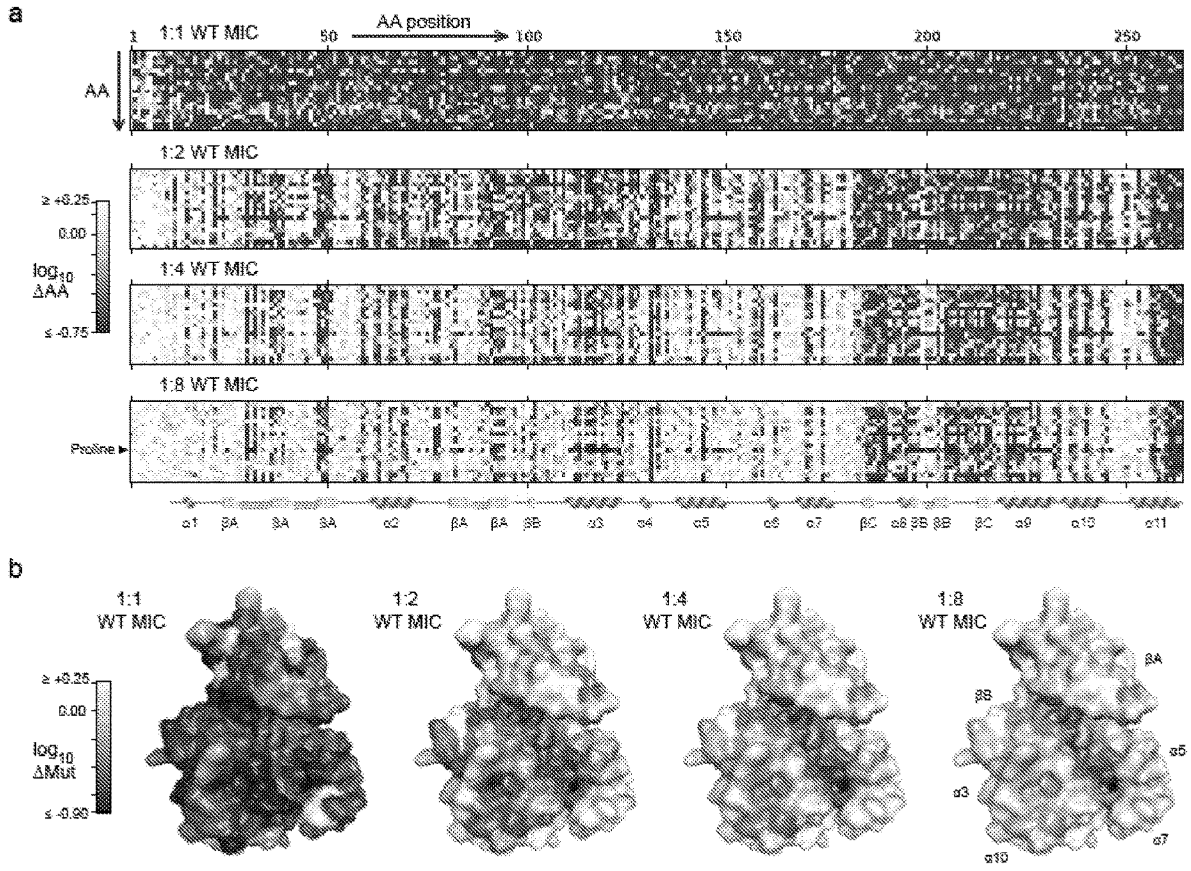
FIG. 11 shows mutational scanning of APH(3')II using neomycin selection. (a) is a series of graphs showing a visual representation of the abundance of each amino acid (ΔAA) at each position after selection at four different concentrations. The shading in each matrix entry corresponds to the change relative to the input library. The known secondary structure of APH(3')II is shown for reference, including alpha helices, beta sheet strands, and beta hairpins (the first 10 residues are unstructured). (b) is a series of projections of the observed changes in the abundance of mutant amino acids (ΔMut) onto a crystal structure of APH('3)II in complex with kanamycin (PDB accession: 1ND4; the kanamycin substrate is not show).
Figure 12:
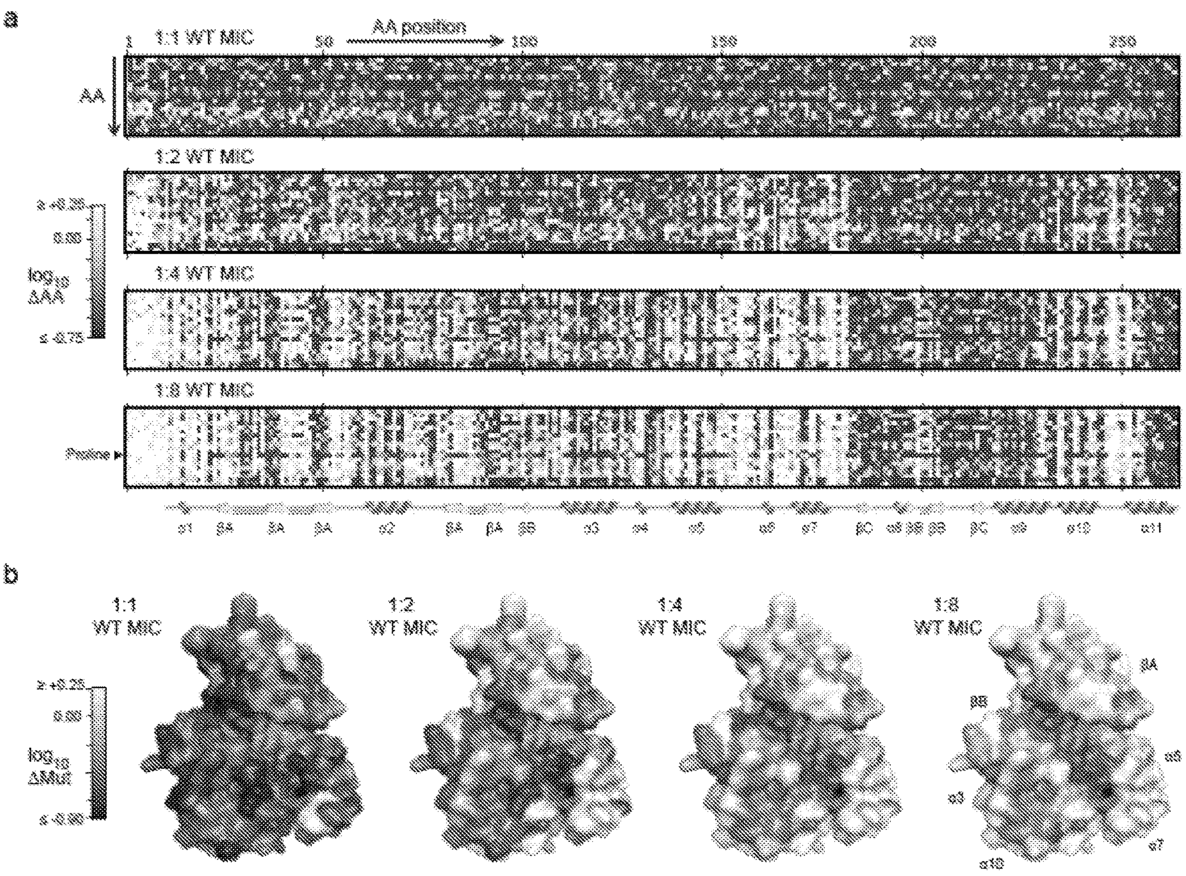
FIG. 12 shows mutational scanning of APH(3')II using paromomycin selection. (a) is a series of graphs showing a visual representation of the abundance of each amino acid (ΔAA) at each position after selection at four different concentrations. The shading in each matrix entry corresponds to the change relative to the input library. The known secondary structure of APH(3')II is shown for reference, including alpha helices, beta sheet strands, and beta hairpins (the first 10 residues are unstructured). (b) is a series of projections of the observed changes in the abundance of mutant amino acids (ΔMut) onto a crystal structure of APH('3)II in complex with kanamycin (PDB accession: 1ND4; the kanamycin substrate is not show).

To compare the selection patterns induced by kanamycin in our experiments to those that have molded APH(3')II over evolutionary timescales, we examined a conservation profile derived from alignment of 133 homologs (Goldenberg, O., Erez, E., Nimrod, G. & Ben-Tal, N. The ConSurf-DB: pre-calculated evolutionary conservation profiles of protein structures. *Nucleic acids research* 37, D323-7 (2009)). We found positive rank correlations between evolutionary conservation and depletion of mutant amino acids at most positions across the protein (from Spearman's ρ=0.51 at ~1:1 WT MIC to ρ=0.74 at 1:8 WT MIC; FIG. 7*a*). The most common discrepancies were positions that were relatively conserved, yet highly tolerant of mutations under selection with kanamycin. For example, we identified 11 conserved residues that consistently tolerated non-WT amino acids even at 1:1 WT MIC (FIG. 7*b*). Interestingly, 7 of the 11 residues directly flank the active site, but none of them appear to interact with kanamycin in the WT enzyme. This may reflect that kanamycin is not the substrate, or at least not the only substrate, that has driven the natural evolution of APH(3')II, and consequently that artificial selection with kanamycin will tolerate or even favor some substitutions that would be deleterious in other contexts.

Figure 13:
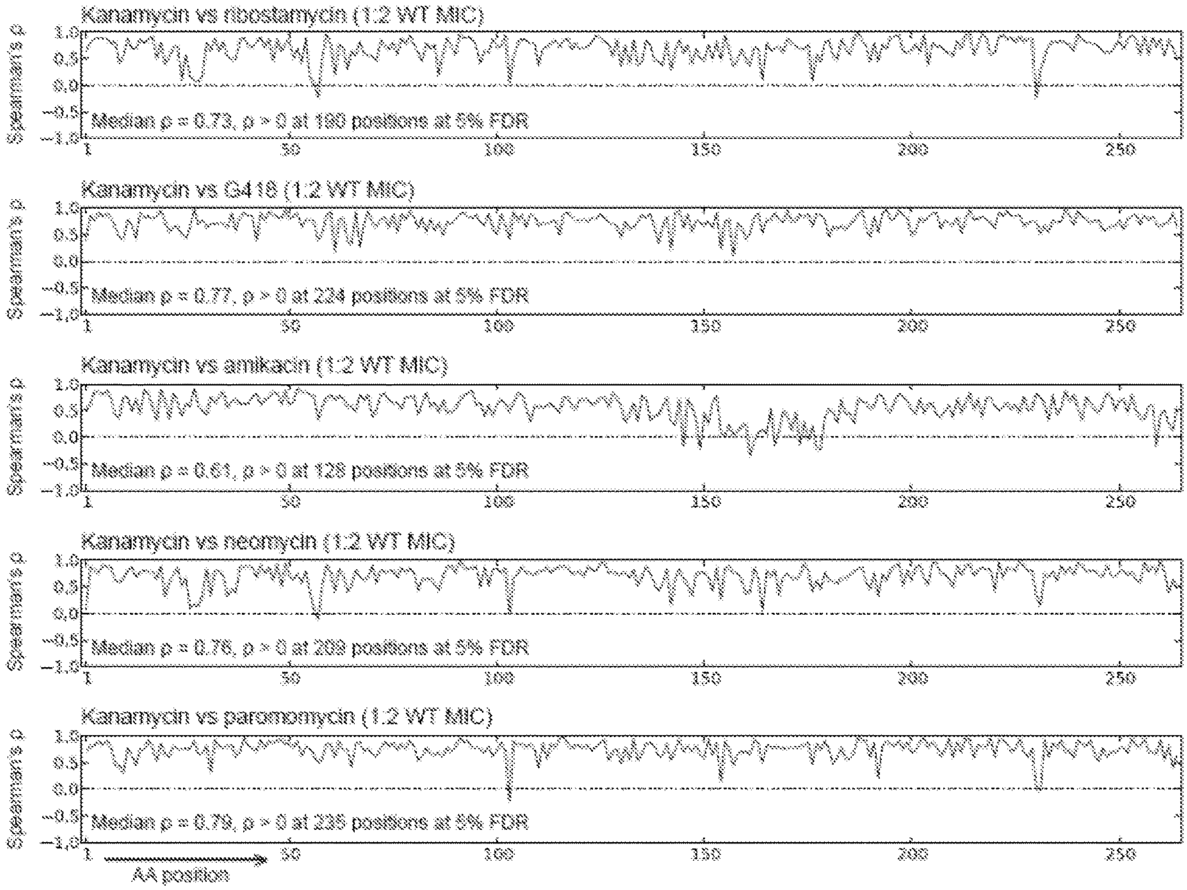
FIG. 13 is a series of graphs of plots of the rank correlation coefficients between the 20 possible amino acids at each position along APH(3')II, after ranking them by the changes in their relative abundances under selection with each indicated pair of aminoglycosides at 1:2 WT MICS.

We next examined the effects of selection using the five other aminoglycosides. These substrates generated concentration- and position-dependent selection patterns that were qualitatively similar to those generated by kanamycin (FIGS. 8-12). To quantitatively compare the patterns, we ranked the twenty amino acids by the relative changes in their abundances after selection and then computed the rank correlations at each position for each pair of conditions. We found that selection with any two aminoglycosides at matched concentrations showed positive correlations at the majority of positions (for example, median Spearman's ρ=0.79 for kanamycin and paromomycin at 1:2 WT MIC and ρ>0 at 235 of 264 positions at 5% FDR; FIG. 13), which implies that the relative fitness values of the mutants were largely similar. We did, however, notice some substitutions that were consistently tolerated under selection with one substrate but depleted under selection with another. We hypothesized that further analysis of these exceptions might identify residues that influence the relative activity of APH (3')II on different substrates.

Figure 14:
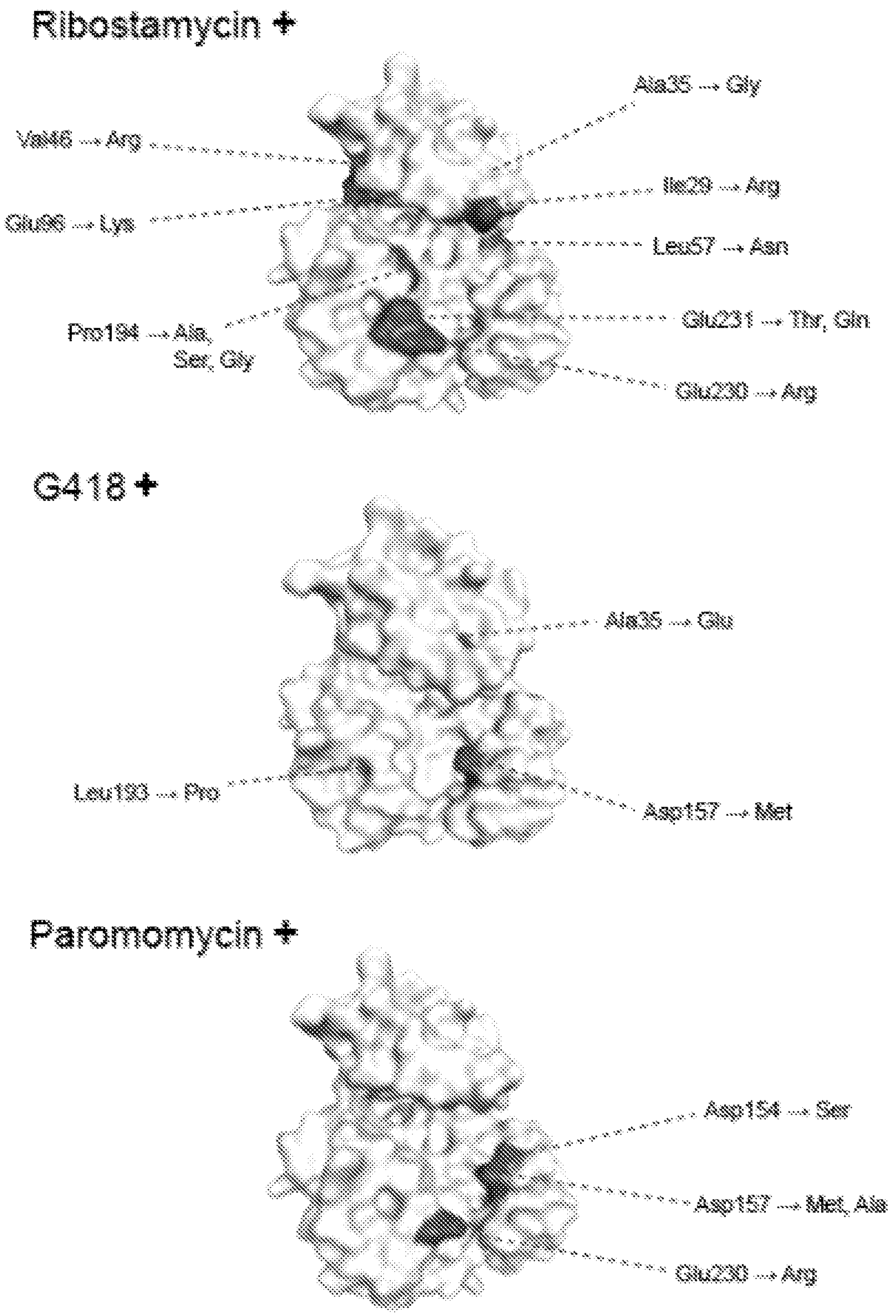
FIG. 14 is a series of images showing positions and identities of amino acid substitutions that appear to be specifically tolerated or favored under selection with the indicated aminoglycoside at its 1:1 WT MIC, but not under selection with kanamycin at its 1:2 WT MIC.

To identify such specificity-determining residues, we queried our data for individual substitutions that showed significant depletion after kanamycin selection at 1:2 WT MIC (at 5% FDR) but no trend towards depletion after selection with a second aminoglycoside at its highest concentration. These stringent criteria identified a handful of substitutions that appeared to be well-tolerated in the presence of ribostamycin, G418 or paromomycin but not kanamycin (11, 3 and 4 single substitutions, respectively; FIG. 14; Table 1). To confirm, we re-synthesized APH(3')II variants containing a selection of these substitutions and compared their specificities towards the second aminoglycoside to that of WT APH(3')II (here, we define specificity as the ratio of the MIC of the second aminoglycoside over the MIC of kanamycin). In six out of nine cases, the tested substitution led to a ≥2-fold increase in specificity towards the second aminoglycoside (range: 2- to 8-fold; see Table 2). Moreover, in nine of eleven additional test cases, we found that combining two or more substitutions that favored the same aminoglycoside increased the specificity to a greater extent than any one of the substitutions did alone (range: 4- to 32-fold; Table 2). This indicates that our approach accurately identified specificity-determining residues in APH(3')II and that these residues can have additive effects.

TABLE 1

Candidate specificity-modifying substitutions

| Selection conditions | Substitutions specfically tolerated under selection with kanamycin | Substitutions specifically tolerated under selection with second aminoglycoside |
|---|---|---|
| G418 at 1:1 WT MIC, Kanamycin at 1:2 WT MIC | n/a | Glu35, Met157, Pro193 |
| G418 at 1:2 WT MIC, Kanamycin at 1:1 WT MIC | None | n/a |
| G418 at 1:2 WT MIC, Kanamycin at 1:2 WT MIC | Glu159, Ile192, Ser227, Arg231, Lys231 | Glu28, Glu31, Phe55, Cys153, Gly154, Thr154, Gln157, Met157, Arg157, Pro160, Pro193, Thr198 |
| Paromomycin at 1:1 WT MIC, Kanamycin at 1:2 WT MIC | n/a | Ser154, Met157, Ala157, Arg230 |
| Paromomycin at 1:2 WT MIC, Kanamycin at 1:1 WT MIC | Lys31 | n/a |
| Paromomycin at 1:2 WT MIC, Kanamycin at 1:2 WT MIC | Lys31, Arg31, Glu159, Ile192, Ser227, Arg231, Phe231, Lys231, Trp231 | Glu31, Ser103, Ala103, Gln154, Gln157, Leu157, Met157, Gly157, Arg230, Asn230 |
| Ribostamycin at 1:1 WT MIC, Kanamycin at 1:2 WT MIC | n/a | Arg29, Gly35, Arg46, Asn57, Lys96, Ser194, Gly194, Ala194, Arg230, Thr231, Gln231 |
| Ribostamycin at 1:2 WT MIC, Kanamycin at 1:1 WT MIC | Ser35, His55 | n/a |
| Ribostamycin at 1:2 WT MIC, Kanamycin at 1:2 WT MIC | Asn27, Ser27, Tyr28, Leu28, Trp35, Gly39, Tyr55, Gln104, Ile192, Tyr255 | Leu27, Ser29, Arg29, Arg46, Asn57, Arg96, Ser101, Arg103, Gly194, Ala194, Arg230, Asn230, Ser231, Gln231, Thr231 |
| Neomycin at 1:1 WT MIC, Kanamycin at 1:2 WT MIC | n/a | None |
| Neomycin at 1:2 WT MIC, Kanamycin at 1:1 WT MIC | His55 | n/a |
| Neomycin at 1:2 WT MIC, Kanamycin at 1:2 WT MIC | Tyr28, Arg31, Pro33, Trp35, Gln104, Glu159, Pro176, Pro178, Val179, Ile192, Arg231, Lys231, Phe231, Trp231 | Asp29, Ser29, Glu31, Trp37, Arg46, Asn56, Asn57, Lys96, Asp194, Gly194 |
| Amikacin at 1:1 WT MIC, Kanamycin at 1:2 WT MIC | n/a | None |
| Amikacin at 1:2 WT MIC, Kanamycin at 1:1 WT MIC | Ile79, Ser127, Phe137, Arg137, Tyr137, Val141, Asn149, Ile149, Phe153, Phe158, Tyr158, Trp158, Tyr163, Phe163, Glu163, Met163, Leu167, Leu173, Asn177, Trp177, Ser177, Ala177, Asp177, Gln177, Leu177, Gly177, Thr177, Tyr177, Phe177, Tyr178, Phe178, Trp256 | n/a |
| Amikacin at 1:2 WT MIC, Kanamycin at 1:2 WT MIC | Phe137, Tyr137, Arg137, Val141, Leu149, Lys149, Asn149, Ile149, Asn151, His151, Phe153, Leu155, Phe158, Tyr158, Trp158, Tyr163, Glu163, Met163, His165, Glu165, Tyr165, Trp165, Phe165, Leu167, Leu168, Glu173, Gln173, Cys175, Pro176, Asn177, Gln177, Ser177, Ala177, Asp177, Tyr177, Leu177, Gly177, Trp177, Thr177, Phe177, Tyr178, Val178, Trp178, His178, Phe178, Gln178, Val179, Thr219, Cys225, Tyr230, Lys249, Try255, Trp256, Tyr256 | Glu35, Val145, Met145, Ile145, Leu145, Cys145, Tyr148, Lys156, Gln157, Glu157, Ile157, Tyr162, Leu162, Trp162, Met162, Ile162, Phe162, Asp168, Ile170, Glu171, Ile174, Arg255, Gln259, Phe259, Thr259, Ala259, Ser259, Trp259, Asp259, His259 |

TABLE 2

Minimum inhibitory concentrations (MICs)
MICs were determined from the A_600 from 2-3 independent cultures using 2-fold dilution series.
The MIC estimated from all matched cultures were identical within the resolution of the assay, expect where a range is shown.
Note that these MICs are higher than those established for selection immediately following transformation
(e.g., Supplementary FIG. 2) due to differences in recovery conditions.

| APH(3')II variant ID | Genotype | Expected phenotype | MIC of kanamycin (ug/mL) | MIC of ribostamycin (ug/mL) | Change in ribostamycin specificity |
|---|---|---|---|---|---|
| KKA2_KLEPN_opt_K1 | Wild-type | n/a | 2000.00 | 15000.00 | n/a |
| KKA2_KLEPN_opt_K13 | Arg230 | Favor ribo. | 250.00-500.00 | 15000.00 | +4- to +8-fold |
| KKA2_KLEPN_opt_K23 | Gly194 | Favor ribo. | 1000.00 | 15000.00 | +2-fold |
| KKA2_KLEPN_opt_K24 | Arg29, Gly35, Arg46, Asn57, Lys96, Gly194, Arg230, Thr231 | Favor ribo. | 15.63-31.25 | 3750.00 | +16- to +32-fold |
| KKA2_KLEPN_opt_K25 (Ribo+) | Leu27, Ser29, Arg46, Asn57, Arg96, Ser101, Arg103, Gly194, Arg230, Ser231 | Favor ribo. | 15.63 | 937.50 | +8-fold |
| KKA2_KLEPN_opt_K26 (Ribo−) | Asn27, Leu28, Trp35, Tyr55, Gln104, Ile192, 255Tyr | Favor kan. | 125.00 | 468.75 | −2-fold |

TABLE 2-continued

Minimum inhibitory concentrations (MICs)
MICs were determined from the A_600 from 2-3 independent cultures using 2-fold dilution series.
The MIC estimated from all matched cultures were identical within the resolution of the assay, expect where a range is shown.
Note that these MICs are higher than those established for selection immediately following transformation
(e.g., Supplementary FIG. 2) due to differences in recovery conditions.

| APH(3')II variant ID | Genotype | Expected phenotype | MIC of kanamycin (ug/mL) | MIC of G418 (ug/mL) | Change in G418 specificity |
|---|---|---|---|---|---|
| KKA2_KLEPN_opt_K1 | Wild-type | n/a | 2000.00 | 50.00 | n/a |
| KKA2_KLEPN_opt_K2 | Glu35 | Favor G418 | 2000.00 | 50.00 | 0 |
| KKA2_KLEPN_opt_K3 | Met157 | Favor G418 | 250.00-500.00 | 25.00-50.00 | +4-fold |
| KKA2_KLEPN_opt_K4 | Pro193 | Favor G418 | 500.00-1000 | 25.00-50 | +2- to +4-fold |
| KKA2_KLEPN_opt_K5 | Glu35, Met157 | Favor G418 | 1000.00 | 100.00 | +4-fold |
| KKA2_KLEPN_opt_K6 | Glu35, Pro193 | Favor G418 | 250.00-500.00 | 25.00 | +2- to +4-fold |
| KKA2_KLEPN_opt_K7 | Met157, Pro193 | Favor G418 | 500.00 | 100.00 | +8-fold |
| KKA2_KLEPN_opt_K8 | Glu35, Met157, Pro193 | Favor G418 | 62.5-125.00 | 25.00 | +8- to +16-fold |
| KKA2_KLEPN_opt_K9 (G418+) | Glu28, Glu31, Phe55, Cys153, Thr154, Arg156, Pro193, 198Thr | Favor G418 | 7.81 | 6.25 | +32-fold |
| KKA2_KLEPN_opt_K10 (G418−) | Glu159, Ile192, Ser227, Arg231 | Favor kan. | 1000.00-2000.00 | 3.13 | −8- to −16-fold |

| APH(3')II variant ID | Genotype | Expected phenotype | MIC of kanamycin (ug/mL) | MIC of amikacin (ug/mL) | Change in amikacin specificity |
|---|---|---|---|---|---|
| KKA2_KLEPN_opt_K1 | Wild-type | n/a | 2000.00 | 25.00 | n/a |
| KKA2_KLEPN_opt_K32 | Ile145 | Favor ami. | 62.50 | 12.50 | +16-fold |
| KKA2_KLEPN_opt_K33 | Tyr148 | Favor ami. | 250.00 | 12.50-25.00 | +4- to +8-fold |
| KKA2_KLEPN_opt_K34 | Lys156 | Favor ami. | 1000.00 | 12.50-25.00 | 0 to +2-fold |
| KKA2_KLEPN_opt_K35 | Ile157 | Favor ami. | 250.00 | 12.50-25.00 | +2- to +4-fold |
| KKA2_KLEPN_opt_K36 | Phe162 | Favor ami. | 125.00 | 12.50-25.00 | +8- to +16-fold |
| KKA2_KLEPN_opt_K37 | Asp168 | Favor ami. | 1000.00 | 12.50-25.00 | 0- to +2-fold |
| KKA2_KLEPN_opt_K38 | Ile170 | Favor ami. | 500.00 | 12.50 | +2-fold |
| KKA2_KLEPN_opt_K39 | Glu171 | Favor ami. | 15.63-31.25 | 12.50-25.00 | +64-fold |
| KKA2_KLEPN_opt_K40 | Ile174 | Favor ami. | 500.00 | 25.00 | +2 fold |
| KKA2_KLEPN_opt_K41 | Arg255 | Favor ami. | 1000.00 | 12.50 | 0 |
| KKA2_KLEPN_opt_K42 | Phe259 | Favor ami. | 62.50 | 25.00-50.00 | +32- to +64-fold |
| KKA2_KLEPN_opt_K43 (Ami+) | Glu35, Ile145, Tyr148, Lys156, Ile157, Phe162, Asp168, Ile170, Glu171, Ile174, Arg255, Phe259 | Favor ami. | 15.63-31.25 | 25.00-50.00 | +128-fold |
| KKA2_KLEPN_opt_K44 (Ami−) | Glu35, Phe137, Val141, Asn149, His151, Phe153, Leu155, Phe158, Phe163, Phe165, Leu167, Leu168, Gln173, Cys175, Pro176, Thr177, Phe177, Val178, Thr219, Cys225, Tyr230, Lys249, Tyr255, Trp256 | Favor kan. | <15.63 | 6.25-12.50 | (*) |

| APH(3')II variant ID | Genotype | Expected phenotype | MIC of kanamycin (ug/mL) | MIC of neomycin (ug/mL) | Change in neomycin specificity |
|---|---|---|---|---|---|
| KKA2_KLEPN_opt_K1 | Wild-type | n/a | 2000.00 | 400.00 | n/a |
| KKA2_KLEPN_opt_K23 | Gly194 | Favor neo. | 1000.00 | 200.00 | 0 |
| KKA2_KLEPN_opt_K27 | Asp194 | Favor neo. | 1000.00 | 200.00 | 0 |
| KKA2_KLEPN_opt_K28 | Ser29, Glu31, Trp37, Arg46, Asn56, Asn57, Lys96, Asp194 | Favor neo. | 31.25 | 50.00-100.00 | +8 to +16-fold |
| KKA2_KLEPN_opt_K29 | Ser29, Glu31, Trp37, Arg46, Asn56, Lys96, Asp194 | Favor neo. | 31.25-62.50 | 100.00-200.00 | +16-fold |
| KKA2_KLEPN_opt_K30 (Neo+) | Ser29, Glu31, Trp37, Arg46, Asn57, Lys96, Asp194 | Favor neo. | 31.25 | 100.00 | +16-fold |
| KKA2_KLEPN_opt_K31 (Neo−) | Tyr28, Arg31, Pro33, Trp35, Gln104, Glu159, Pro176, Pro178, Val179, Ile192, Trp231 | Favor kan. | 62.50 | 6.25-12.50 | 0 to −2-fold |

| APH(3')II variant ID | Genotype | Expected phenotype | MIC of kanamycin (ug/mL) | MIC of paromomycin (ug/mL) | Change in paromomycin specificity |
|---|---|---|---|---|---|
| KKA2_KLEPN_opt_K1 | Wild-type | n/a | 2000.00 | 4000.00 | n/a |
| KKA2_KLEPN_opt_K3 | Met157 | Favor paro. | 500.00 | 2000.00-4000.00 | +2- to +4-fold |

TABLE 2-continued

Minimum inhibitory concentrations (MICs)
MICs were determined from the A_600 from 2-3 independent cultures using 2-fold dilution series.
The MIC estimated from all matched cultures were identical within the resolution of the assay, expect where a range is shown.
Note that these MICs are higher than those established for selection immediately following transformation
(e.g., Supplementary FIG. 2) due to differences in recovery conditions.

| | | | | | |
|---|---|---|---|---|---|
| KKA2_KLEPN_opt_K11 | Ser154 | Favor paro. | 1000.00 | 2000.00-4000.00 | 0 to +2-fold |
| KKA2_KLEPN_opt_K12 | Ala157 | Favor paro. | 1000.00 | 2000.00-4000.00 | 0 to +2-fold |
| KKA2_KLEPN_opt_K13 | Arg230 | Favor paro. | 250.00-500.00 | 8000.00 | +8- to +16-fold |
| KKA2_KLEPN_opt_K15 | Ser154, Met157 | Favor paro. | 250.00-500.00 | 2000.00-4000.00 | +4-fold |
| KKA2_KLEPN_opt_K16 | Ser154, Arg230 | Favor paro. | 125.00 | 4000.00-8000.00 | +16- to +32-fold |
| KKA2_KLEPN_opt_K17 | Ala157, Arg230 | Favor paro. | 125.00 | 2000.000-4000 | +8- +16-fold |
| KKA2_KLEPN_opt_K18 | Met156, Arg230 | Favor paro. | 125.00 | 2000.00-4000.00 | +8- to +16-fold |
| KKA2_KLEPN_opt_K19 | Ser154, Met157, Arg230 | Favor paro. | 31.25-62.50 | 2000.00-4000.00 | +16- to +32-fold |
| KKA2_KLEPN_opt_K20 | Ser154, Ala157, Arg230 | Favor paro. | 62.50 | 2000.00 | +16-fold |
| KKA2_KLEPN_opt_K21 (Paro+) | Glu31, Ala103, Gln154, Met157, Arg230 | Favor paro. | 31.25 | 2000.00-4000.00 | +16- to +32-fold |
| KKA2_KLEPN_opt_K22 (Paro−) | Lys31, Glu159, Ile192, Ser227, Lys231 | Favor kan. | 2000.00 | 62.50 | −64-fold |

(*) 12.5 ug/mL was the lowest amikacin concentration that reliably inhibited growth of untransformed *e. coli* in this experiment. These estimated MICs therefore reflect total or near total loss of activity on both susbtrates.

Figure 15:
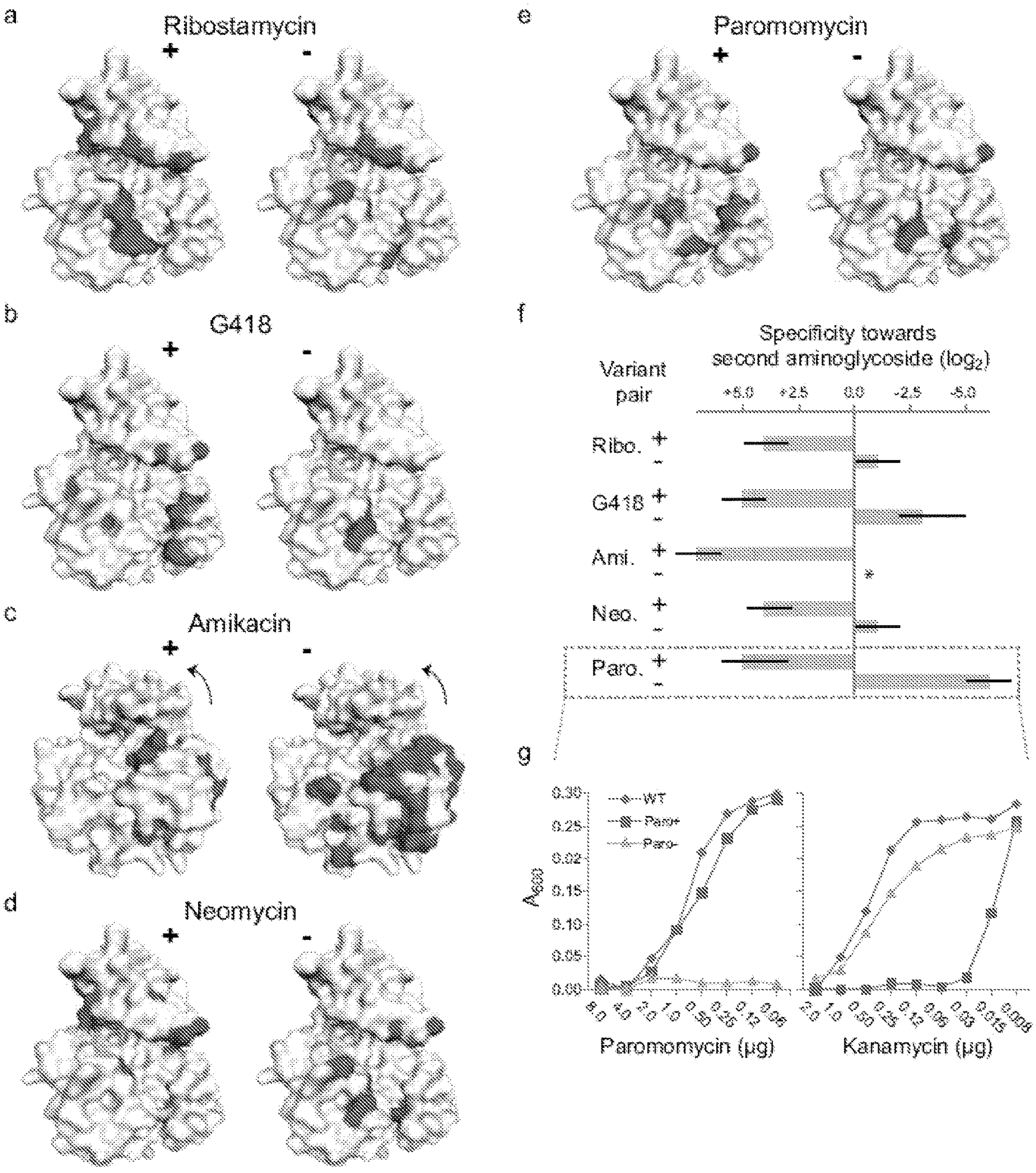
FIG. 15 shows identification of specificity-determining residues in APH(3')II. (a)-(e) are a series of images showing the positions of substitutions that are specifically tolerated (+) or depleted (−) under selection with the indicated aminoglycoside relative to selection with kanamycin shaded.

To expand our search for specificity-determining residues, we next looked for substitutions that showed significant depletion after kanamycin selection at 1:2 WT MIC (at 5% FDR) but no trend towards depletion by the second aminoglycoside at its 1:2 WT MIC, or vice versa. These less stringent criteria identified additional candidates in every pairwise comparison (FIG. 15*a-e*; Table 1). Many of these candidate substitutions flanked the active site, particularly at or near residues that interact with the second and third ring of kanamycin in the WT crystal structure (in particular, the α5-α7 and α9-α10 helices). This is an expected hotspot for specificity-determining residues, because the first ring is constrained by being the phosphate acceptor, while the remaining rings show significant structural diversity among the aminoglycosides (Nurizzo, D. et al. The Crystal Structure of Aminoglycoside-3'-Phosphotransferase-IIa, an Enzyme Responsible for Antibiotic Resistance. *Journal of Molecular Biology* 327, 491-506 (2003)). Candidate substitutions were also frequently found in a relatively flexible part of the N-terminal domain that extends over the phosphate donor (ATP) and aminoglycoside binding sites (in particular, positions 27-57), and in the linker region between the N-terminal domain and the central core (in particular, position 96). These substitutions may influence the presentation of the two substrates near the catalytic residue, but the absence of ATP in the crystal structure limits potential insights from the available model. To confirm the expected functional effects of the identified substitutions, we synthesized and determined the substrate-specificity of five pairs of designed APH(3')II variants, where each pair incorporated all substitutions that were preferentially tolerated by either kanamycin or, the second aminoglycoside in the respective comparison (if multiple candidate substitutions were found at one position, we picked the one that showed the largest difference in abundance). Nine of the ten tested variants showed changes in specificity that favored the targeted substrate (range: 2- to 128-fold; FIG. 15*f* and Table 2). The tenth variant had minimal activity on both substrates, which was likely a consequence of the relatively large number of substitutions in this variant (24 compared to 12 or less in the others). Indeed, in six of the nine successful cases, the expected increase in specificity also came with a concomitant but lesser decrease in absolute activity (as measured by the relevant MIC; Table 2), which suggests a precarious balance between the two properties. Strikingly, the two variants that were designed to favor or disfavor paromomycin relative to kanamycin showed a >2,000-fold combined change in their specificities. In this case, a single round of tiling mutagenesis was therefore sufficient to derive two synthetic enzyme variants with essentially orthogonal substrate specificities from one non-specific progenitor (FIG. 15*g*).

In summary, tiling mutagenesis coupled with deep sequencing allowed us to perform quantitative mutational scanning of the complete APH(3')II protein coding sequence with sufficient accuracy to identify individual kinase activity- and substrate specificity-determining residues. We emphasize that structural information was not required or directly utilized to identify these residues. Our approach is therefore applicable even when accurate structural models are not available. Assuming that indirect selection strategies can be devised, it can also be extended to proteins and activities that do not confer a direct growth advantage. Notably, we have recently used a similar approach to identify activity- and specificity-determining nucleotides in mammalian gene regulatory elements (Melnikov, A. et al. Systematic dissection and optimization of inducible enhancers in human cells using a massively parallel reporter assay. *Nature biotechnology* 30, 271-7 (2012)). In both cases, we found that combining mutational scanning data from two separate conditions is an effective method for identifying mutations that change the ratio of the activities in the two conditions in the desired direction.

Methods

Plasmid Construction and Cloning

Primers and individual oligonucleotides were synthesized by Integrated DNA Technologies (Coralville, Iowa), the two 200 mer oligonucleotide pools containing mutagenesis tiles were synthesized by Agilent (Santa Clara, Calif.) as previously described (LeProust, E. M. et al. Synthesis of high-quality libraries of long (150mer) oligonucleotides by a novel depurination controlled process. *Nucleic acids research* 38, 2522-40 (2010)), the WT APH(3')II coding region template for library construction was synthesized by GenScript USA (Piscataway, N.J.), and the single- and multi-substitution synthetic ORF variants for validation of specificity-determining amino acid residues were synthesized by Gen9 (Cambridge, Mass.).

To generate a plasmid vector carrying a constitutive EM7 promoter (Life Technologies) and a synthetic gene encoding APH('3)II (neo; UniProtKB entry name: KKA2_KLEPN) flanked by two SacI restriction sites, we first combined a DNA fragment containing EM7 (template: EM7_pBR322; primers: EM7_Amp_F/R) with a PCR-linearized pBR322 backbone (template: pBR322; primers: pBR322_EM7_F/R) using the In-Fusion PCR Cloning System (Clontech Laboratories, Mountain View, Calif.). The resulting plasmid (pBR322[EM7]) was then re-linearized by inverse PCR (primers: pBR322_tetRLin_F/R) and combined with a PCR amplified neo ORF fragment (template: KKA2_KLEPN_opt; primers: KKA2_pBR322_F/R) by In-Fusion to replace the tetR ORF of pBR322 with neo. The final product (pBR322[EM7-neo]) was isolated using QIAprep Spin Miniprep kits (Qiagen, Gaitehrsburg, Md.) and verified by Sanger sequencing (primers: pBR322_Seq_F/R).

To generate the APH('3)II single-substitution libraries, full-length oligonucleotides were first isolated from the synthesized pools using 10% TBE-Urea polyacrylamide gels (Life Technologies, Carlsbad, Calif.). Each pair of APH(3')II tiles and corresponding linearized pBR322[EM7-neo] plasmids were PCR amplified by Herculase II DNA Polymerase (Agilent) with their respective primers (primer prefix: KKA2_TileAmp for tiles, KKA2_LinAmp for backbones), size selected on 1% E-Gel EX agarose gels (Life Technologies), purified with MinElute Gel Extraction kits (Qiagen) and combined using In-Fusion reactions. Each reaction was separately transformed into Stellar chemically competent cells (Clontech), the transformants were grown in LB media with carbenicillin (50 μg/mL) and plasmid DNA libraries were isolated using QIAprep Spin Miniprep kits (Qiagen). Finally, complete substitution libraries were generated by pooling equimolar amounts of the resulting six single-tile plasmid libraries.

To generate plasmids encoding selected single- and multiple-substitution APH(3')II variants, we amplified the Gen9 synthetic ORFs using Herculase II DNA Polymerase (primers: KKA2_pBR322_F/R) and inserted them into a PCR-linearized backbone (primers: pBR322_tetLin_F/R, template: pBR322[EM7]) using In-Fusion reactions. The resulting plasmids (pBR322[EM7-K1] through pBR322 [EM7-K44]) were verified by Sanger sequencing and preserved in *E. coli* as glycerol stock.

Cell Culture and Selection

To determine the minimum inhibitory concentration (MIC) of each of the six aminoglycosides: kanamycin, ribostamycin, G418, amikacin, neomycin, paromomycin (Sigma-Aldrich, St. Louis, Mo.) in *E. coli* expressing WT APH(3')II, Stellar cells were transformed with pBR322-EM7-neo, recovered in SOC medium (New England Biolabs (NEB), Ipswich, Mass.) at 37° C. for 1 hr, diluted 1:100 with LB and then divided into 96-well growth blocks containing LB with carbenicillin (50 μg/mL) and 2-fold serial dilutions of aminoglycosides. After growth at 37° C. with shaking for 24 hrs, the culture densities were assessed by absorbance at 600 nm ($A_{600}$) using a NanoDrop 8000 (Thermo Scientific, Billerica, Mass.). The MIC for each aminoglycoside was estimated as the lowest dilution at which $A_{600}$ was less than 0.025.

To perform mutational scanning, Stellar cells were transformed with 10 ng (~3 fmol) of mutant library plasmids, recovered in SOC medium at 37° C. for 1 hour, diluted into 15 mL LB with carbenicillin (50 μg/mL) and one of the aminoglycosides at 1:1, 1:2, 1:4 or 1:8 dilutions of the following concentrations (estimated 1:1 WT MICs): 225 μg/mL for kanamycin, 2500 μg/mL for ribostamycin, 5 μg/mL for G418, 10 μg/mL for amikacin, 40 μg/mL for neomycin and 320 μg/mL for paromomycin. The cultures were incubated in 50 mL tubes at 37° C. with shaking for 24 hours, pelleted by centrifugation and frozen at −20° C. Plasmids were isolated from the pellets using QIAprep Spin Miniprep kits (Qiagen). Each transformation and selection was performed in duplicate, using each of the two independently generated mutant libraries.

To establish the substrate specificity of the synthetic APH(3')II variants relative to WT APH(3')II, glycerol stocks of the relevant clones (pBR322[EM7-K1] through pBR322 [EM7-K44]) were streaked onto LB agar plates and cultured overnight at 37° C. Single colonies were then inoculated into 1 mL LB with 50 μg carbenicillin, incubated at 37° C. with shaking for 6 hours, diluted 1:100 into LB media, and then split into 96-well deep well plates containing LB with carbenicillin (50 μg/mL) and 2-fold serial dilutions of aminoglycosides dilution series. We note that the longer recovery in these follow-up experiments increased the absolute MICs compared to those we measured immediately following transformation).

Mut-Seq

To sequence and count mutations, the APH(3')II coding regions were first isolated from the plasmid pools by SacI digest (NEB) followed by agarose gel purification. The SacI fragments were ligated into high molecular weight concatemers using T4 DNA ligase (NEB). The concatemers were fragmented and converted to sequencing libraries using Nextera DNA Sample Prep kits (Illumina, San Diego Calif.). Library fragments from the 200-800 nt size range were selected using agarose gels and then sequenced on Illunnina MiSeq instruments using 2×150 nt reads. The reads were subsequently aligned to a reference sequence consisting of concatenated copies of the WT APH(3')II coding region using BWA version 0.5.9-r16 with default parameters (Li, H. & Durbin, R. Fast and accurate short read alignment with Burrows-Wheeler transform. *Bioinformatics* 25, 1754-60 (2009)). The number of occurrences of each amino acid at each position along the coding region was then counted and tabulated from the aligned reads. Only codons for which all three sequenced and aligned nucleotides had phred quality scores ≥30 were included in these counts.

Computational Analysis

Data processing and statistical analysis, including computation of Pearson's and Spearman's correlation coefficients, $x^2$-statistics and associated p-values, were performed using the Enthought Python Distribution (www.enthought.com), with IPython (Pérez, F. & Granger, B. E. IPython: A System for Interactive Scientific Computing. *Computing in Science & Engineering* 9, 21-29 (2007)), NumPy version 1.6.1, SciPy version 0.10.1 and matplotlib version 1.1.0 (Hunter, J. D. Matplotlib: A 2D graphics environment. *Computing in Science & Engineering* 9, 90-95 (2007)). Rendering of the APH(3')II crystal structure (PDB accession 1ND4) was performed using PyMOL version 1.5 (Schrödinger). The rendering of its secondary structure was derived from PDBsum at EMBL-EB (www.ebi.ac.uk/pdbsum/). The evolutionary conservation profile for APH (3')II was obtained from ConSurf-DB (Goldenberg, O., Erez, E., Nimrod, G. & Ben-Tal, N. The ConSurf-DB: pre-calculated evolutionary conservation profiles of protein structures. *Nucleic acids research* 37, D323-7 (2009)).

The magnitude of changes in the abundance of mutant amino acids at each position after selection was estimated as $$\Delta Mut=(Mut_{selected}/WT_{selected})/(Mut_{input}/WT_{input})$$

where $Mut_{input}$ and $WT_{input}$ are, respectively, the observed counts of mutant and wild-type amino acids at that position in the input library and $Mut_{selected}$ and $WT_{selected}$ are the corresponding observed counts after selection.

The magnitude of changes in the abundance of each specific amino acid at each position after selection was estimated as $$\Delta AA=(AA_{selected}/\neg AA_{selected})/(AA_{input}/\neg AA_{input})$$

where $AA_{input}$ and $\neg AA_{input}$ are, respectively, the observed counts of that amino acid and all other amino acids at that position in the input library and $AA_{selected}$ and $\neg AA_{selected}$ are the corresponding observed counts after selection.

The statistical significance of a deviation of any ΔMut or ΔAA from 1.0 was estimated using a $\chi^2$-test for independence on a 2×2 contingency table that contained the four corresponding counts with a pseudocount of 1 added to each. To correct for multiple hypothesis testing, the Benjamini-Hochberg procedure was applied to identify the 5% false discovery rate (FDR) threshold (Benjamini, Y. & Hochberg, Y. Controlling the false discovery rate: a practical and powerful approach to multiple testing. *Journal of the Royal Statistical Society. Series B.* 57, 289-300 (1995)). We note that ΔMut or ΔAA values greater than 1.0 do not necessarily indicate higher fitness relative to the WT APH(3')II (i.e., positive selection), because the majority of ORFs that contributed to the count of WT residues at one position still carried substitutions at other positions.

Substitutions that favored growth under selection with one aminoglycoside relative to another were identified by requiring $\Delta AA<1.0$ at 5% FDR across two replicates under selection with the first and $\Delta AA\geq1.0$ across two replicates for the same substitution under selection with the other, as well as a minimum difference of 0.5 between the $\log_{10}$-transformed ΔAA values, at the concentrations indicated in the main text. These thresholds were established empirically to select a limited number of high confidence candidates.

Variants Implicated in Rosiglitazone-Dependent Adipocyte Differentiation

We also designed an experiment to determine which amino acid residues in PPARγ are implicated in rosiglitazone-dependent adipocyte differentiation. Using a method similar to that described above, we synthesized a mutant library containing variants of the PPARγ gene. This library was cloned into inducible lentiviral vectors. We transduced Simpson-Golabi-Behemel Syndrome (SGBS) pre-adipocytes at a multiplicity of infection of approximately 0.3. Transduced cells were then selected and expanded in the presence of puromycin followed by the induction of differentiation in the presence of doxycycline (to induce expression of PPARγ from the lentiviral vector) and the PPARγ agonist rosiglitazone. Differentiation was selected for by separation of cells by CD36 expression. The DNA contents of the selected populations of cells was sequenced and identification of PPARγ variants enriched and depleted in CD36+ cells was performed (FIGS. 16-19).

Other Embodiments

From the foregoing description, it will be apparent that variations and modifications may be made to the invention described herein to adopt it to various usages and conditions. Such embodiments are also within the scope of the following claims.

All publications, patent applications, and patents mentioned in this specification are herein incorporated by reference to the same extent as if each independent publication, patent application, or patent was specifically and individually indicated to be incorporated by reference.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. A method of generating a mixture of variants of a template DNA molecule, said method comprising:

a) providing a plurality of oligonucleotides synthesized on one or more solid supports comprising one or more sets of oligonucleotides, each set corresponding to one of multiple ("n") 100 to 500 nucleotide regions of said template DNA molecule, wherein the oligonucleotides in each set of oligonucleotides comprise:

i) 5' and 3' ends identical to the 5' and 3' ends of the region, and ii) a central variable region comprising at least one sequence variation as compared to the sequence of said region of said template DNA molecule and the other oligonucleotides in the set;

b) amplifying a set of oligonucleotides on the one or more solid supports corresponding to a first region of said template DNA molecule from the plurality of oligonucleotides using polymerase chain reaction (PCR);

c) providing a plurality of linearized plasmid vectors comprising the template DNA molecule, but lacking said first region of said template DNA molecule, wherein said plurality of linearized plasmid vectors is generated by polymerase chain reaction using primers having 5' ends that are facing each other on the vector and 3' ends oriented such that extension amplifies the entire sequence of the vector except for the first region, wherein the ends of said linearized plasmid vectors are configured for joining with the ends of the amplified set of oligonucleotides to complete the template DNA molecule; and d) joining said amplified set of oligonucleotides to said plurality of linearized plasmid vectors, thereby generating a mixture of circular plasmids comprising a mixture of variants of said first region of said template DNA molecule.

2. The method of claim 1, wherein said template DNA molecule encodes a polypeptide, a non-coding RNA, an untranslated regulatory sequence, a promoter sequence, and/or an enhancer sequence.

3. The method of claim 1, wherein said variation is a substitution or deletion of at least one nucleotide.

4. The method of claim 1, further comprising repeating steps b) to d) for a second region of said template DNA molecule; and e) mixing said mixture of circular plasmids comprising variants of said first region of said template DNA molecule with said mixture of circular plasmids comprising variants of said second region of said template DNA molecule to generate a mixture of variants of said first and second regions of said template DNA molecule.

5. The method of claim 1, wherein each of the one or more sets of oligonucleotides of step (a) is a set of oligonucleotides that encodes at least one variation of every amino acid encoded by the central variable region of the set of oligonucleotides.

6. The method of claim 1, wherein each of the one or more sets of oligonucleotides of step (a) is a set of oligonucleotides that comprises at least one variation of every nucleotide of the central variable region of the set of oligonucleotides, and/or is a set of oligonucleotides that each have variation in more than one nucleotide of the central variable region.

7. The method of claim 1, wherein said method further comprises repeating steps b) to d) for each of said "n" regions to generate a mixture of circular plasmids, wherein each mixture of circular plasmids has variants of one of said "n" regions of said template molecule; and e) mixing each mixture of circular plasmids to generate a mixture of circular plasmids having variants of said "n" regions of said template DNA molecule.

8. The method of claim 5, wherein said at least one variation of every amino acid is at least one naturally occurring variation of every amino acid.

9. The method of claim 1, further comprising:

e) transforming said mixture of circular plasmids generated by said joining into a host cell;

f) selecting for recombinant clones containing said plasmids; and g) isolating said plasmids containing said variants.

10. A method of generating a mixture of variants of a template DNA molecule, said method comprising:

a) providing a plurality of oligonucleotides synthesized on one or more solid supports comprising two or more sets of oligonucleotides, each set corresponding to one of multiple ("n") 100 to 500 nucleotide consecutive regions of said template DNA molecule, wherein the oligonucleotides in each set of oligonucleotides comprise:

i) 5' and 3' ends identical to the 5' and 3' ends of the region, and ii) a central variable region comprising at least one sequence variation as compared to the sequence of said region of said template DNA molecule and the other oligonucleotides in the set;

b) amplifying two or more sets of oligonucleotides on the one or more solid supports corresponding to consecutive multiple regions of said template DNA molecule from the plurality of oligonucleotides using polymerase chain reaction (PCR);

c) providing a plurality of linearized plasmid vectors comprising the template DNA molecule, but lacking said consecutive multiple regions of said template DNA molecule, wherein said plurality of linearized plasmid vectors is generated by polymerase chain reaction using primers having 5' ends that are facing each other on the vector and 3' ends oriented such that extension amplifies the entire sequence of the vector except for the consecutive multiple regions, wherein the ends of said linearized vectors are configured for joining with the ends of the amplified sets of oligonucleotides corresponding to the two outermost of the consecutive multiple regions of said template DNA molecule to complete the template DNA molecule upon joining of all of said amplified plurality of oligonucleotides corresponding to consecutive multiple regions; and d) joining said amplified sets of oligonucleotides to each other and said plurality of linearized plasmid vectors, thereby generating circular plasmids comprising a mixture of variants of said multiple regions of said template DNA molecule.

11. A method of identifying a variant nucleic acid molecule which, when introduced into a cell, selectively increases or decreases the sensitivity of the cell to an environmental factor, said method comprising:

a) introducing a mixture of variants of a template DNA molecule into both a first population of cells and a second population of cells, wherein said mixture of variants of a template DNA molecule are generated by the methods of claim 1, b) incubating said first population of cells in the presence of a first environmental factor;

c) incubating said second population of cells in the absence of said first environmental factor;

d) isolating cells exhibiting a phenotype associated with increased or decreased sensitivity to said first environmental factor; and e) determining which variants of said template DNA molecule are enriched or depleted in cells isolated from said first population of cells as compared to said second population of cells; thereby identifying a variant nucleic acid that selectively increases or decreases the sensitivity of said cells to said first environmental factor.

12. The method of claim 11, wherein said second population of cells are grown in the presence of a second environmental factor, thereby identifying a variant that selectively increases or decreases the sensitivity of said cells to said first environmental factor relative to said second environmental factor.

13. The method of claim 11, wherein said isolating of cells comprises collection of surviving cells, separation of cells having a morphological characteristic, optionally wherein said morphological characteristic is cell size, expression of a differentiation marker, cell adhesion, or cell membrane integrity, and/or fluorescent activation cell sorting (FACS).

14. The method of claim 11, further comprising introducing a mixture of variants of a template DNA molecule into a third population of cells, incubating said third population of cells in the presence of a third environmental factor, and determining which variants of said template DNA molecule are enriched or depleted in cells incubated with said third environmental factor compared to said first and/or second environmental factors, thereby identifying variants that selectively increase or decrease sensitivity of said cells to said third environmental factor.

15. The method of claim 11, wherein said mixture of variants of a template DNA molecule are encapsulated in a viral particle when introduced into said population of cells.

16. The method of claim 15, wherein said isolating cells exhibiting a phenotype associated with increased or decreased sensitivity to said first environmental factor further comprises isolating viral DNA or RNA from said population of cells.

17. The method of claim 1, wherein the plurality of oligonucleotides is synthesized on separate solid supports.

18. The method of claim 1, wherein the central variable regions of each of the one or more sets of oligonucleotides collectively span the entire template DNA molecule.

* * * * *

UNITED STATES PATENT AND TRADEMARK OFFICE

CERTIFICATE OF CORRECTION

PATENT NO. : 11,274,295 B2

APPLICATION NO. : 14/420881

DATED : March 15, 2022

INVENTOR(S) : Tarjei Mikkelsen and Alexandre Melnikov

It is certified that error appears in the above-identified patent and that said Letters Patent is hereby corrected as shown below:

In the Specification

Column No. 2, Line No. 65, “plasm id” should be -- plasmid --
Column No. 3, Line No. 25, “‘in’” should be -- ‘n’ --
Column No. 3, Line No. 60, “cells,” should be -- cells; --
Column No. 6, Line No. 61, “carbencillin” should be -- carbenicillin --
Column No. 9, Line Nos. 20-21, “rosigliatizone” should be -- rosiglitazone --
Column No. 12, Line No. 5, “carabenicillin” should be -- carbenicillin --
Column No. 12, Line No. 10, “plasm ids” should be -- plasmids --
Column No. 13, Line No. 23, “apectinomycin” should be -- spectinomycin --
Column No. 13, Line No. 47, “Oxazolidonones” should be -- Oxazolidinones --
Column No. 14, Line No. 23, “panitumab” should be -- panitumumab --
Column No. 14, Line No. 42, “balavir” should be -- balvir --
Column No. 14, Line Nos. 55-56, “pyramidine” should be -- pyrimidine --
Column No. 16, Line No. 31, “salsalate)” should be -- - salsalate). --
Column No. 16, Line No. 45, “Sulphonanilides” should be -- Sulphonamides --
Column No. 17, Line No. 7, “the an” should be -- the --
Column No. 19, Line No. 61, “asparginine” should be -- asparagine --
Column No. 21, Line No. 3 (approx.), “specfically” should be -- specifically --
Column No. 25, Line No. 21 (approx.), “susbtrates” should be -- substrates --
Column No. 25, Line No. 53, “or,” should be -- or --
Column No. 27, Line No. 12, “Gaitehrsburg,” should be -- Gaithersburg --
Column No. 28, Line No. 29, “Illunnina” should be -- Illumina --
Column No. 29, Line No. 46, “Golabi-Behemel” should be -- Golabi-Behmel --

Signed and Sealed this
Twenty-eighth Day of June, 2022

Katherine Kelly Vidal

Katherine Kelly Vidal
*Director of the United States Patent and Trademark Office*